(12) United States Patent
Sexton et al.

(10) Patent No.: US 12,111,964 B2
(45) Date of Patent: Oct. 8, 2024

(54) DRIVE MANAGER FOR POWER WHEELCHAIR AND RELATED METHODS

(71) Applicant: LifeDrive LLC, South Bend, IN (US)

(72) Inventors: John Patrick Sexton, Cumming, GA (US); Shawn Patrick Sexton, Cumming, GA (US); Mary Kathryn Bryson Sexton, Cumming, GA (US)

(73) Assignee: Life Drive LLC, Cumming, GA (US)

( * ) Notice: Subject to any disclaimer, the term of this patent is extended or adjusted under 35 U.S.C. 154(b) by 0 days.

(21) Appl. No.: 18/036,228

(22) PCT Filed: Oct. 28, 2022

(86) PCT No.: PCT/US2022/048190
§ 371 (c)(1),
(2) Date: May 10, 2023

(87) PCT Pub. No.: WO2023/076573
PCT Pub. Date: May 4, 2023

(65) Prior Publication Data
US 2024/0019930 A1    Jan. 18, 2024

Related U.S. Application Data

(60) Provisional application No. 63/272,842, filed on Oct. 28, 2021.

(51) Int. Cl.
*G06F 3/01* (2006.01)
*A61G 5/04* (2013.01)

(52) U.S. Cl.
CPC ............... *G06F 3/013* (2013.01); *A61G 5/04* (2013.01); *A61G 2203/18* (2013.01)

(58) Field of Classification Search
CPC ....... G06F 3/013; A61G 5/04; A61G 2203/18; A61G 5/00; A61B 3/113
See application file for complete search history.

(56) References Cited

U.S. PATENT DOCUMENTS

2019/0052637 A1* 2/2019 Dean .................... H04W 12/04
2020/0022577 A1* 1/2020 Rishoni .............. G02B 27/0172
(Continued)

FOREIGN PATENT DOCUMENTS

CN        111297581 A     6/2020

OTHER PUBLICATIONS

Eid Mohamad a et al: "A Novel Eye-Gaze-Controlled Wheelchair System for Navigating Unknown Environments: Case Study with a Person With ALS", IEEE Access, vol. 4, Jan. 28, 2016 (Jan. 28, 2016), pp. 558-573, XP011602373, DOI: 10.1109/ACCESS.2016. 2520093.

(Continued)

*Primary Examiner* — Matthew A Eason
*Assistant Examiner* — Chayce R Bibbee
(74) *Attorney, Agent, or Firm* — Wood Herron & Evans LLP

(57) ABSTRACT

A power wheelchair [4] includes moveable components, motors, a drive controller [6] operatively connected to the motors, and a drive manager device [8] operatively connected to the drive controller [6]. The drive manager device [8] is configured to communicate with an input collection/display unit (IC/DU) 10 via a first communication interface, the IC/DU [10] operable by a user in the power wheelchair. The drive manager device [8] is configured to communicate with a caregiver unit [12] via a second communication interface, the caregiver unit [12] operable by a caregiver. The drive manager device [8] is configured to determine a command made by the user or the caregiver by processing command data received in a communication with the IC/DU [10] or the caregiver unit [12]. The drive manager device [8] is configured to cause voltage to be applied to the drive controller [6] to cause the drive controller [6] to interact with (Continued)

the motors to actuate at least one of the moveable components.

17 Claims, 17 Drawing Sheets

(56) References Cited

U.S. PATENT DOCUMENTS

| | | | |
|---|---|---|---|
| 2020/0077264 A1* | 3/2020 | Studer | H04L 63/105 |
| 2021/0093495 A1* | 4/2021 | Kelly | A61G 5/1075 |
| 2021/0259601 A1 | 8/2021 | Kornberg et al. | |

OTHER PUBLICATIONS

European Patent Office, International Search Report and Written Opinion of the International Searching Authority, International Application No. PCT/US2022/048190, mailed Feb. 2, 2023 (10 pages).

* cited by examiner

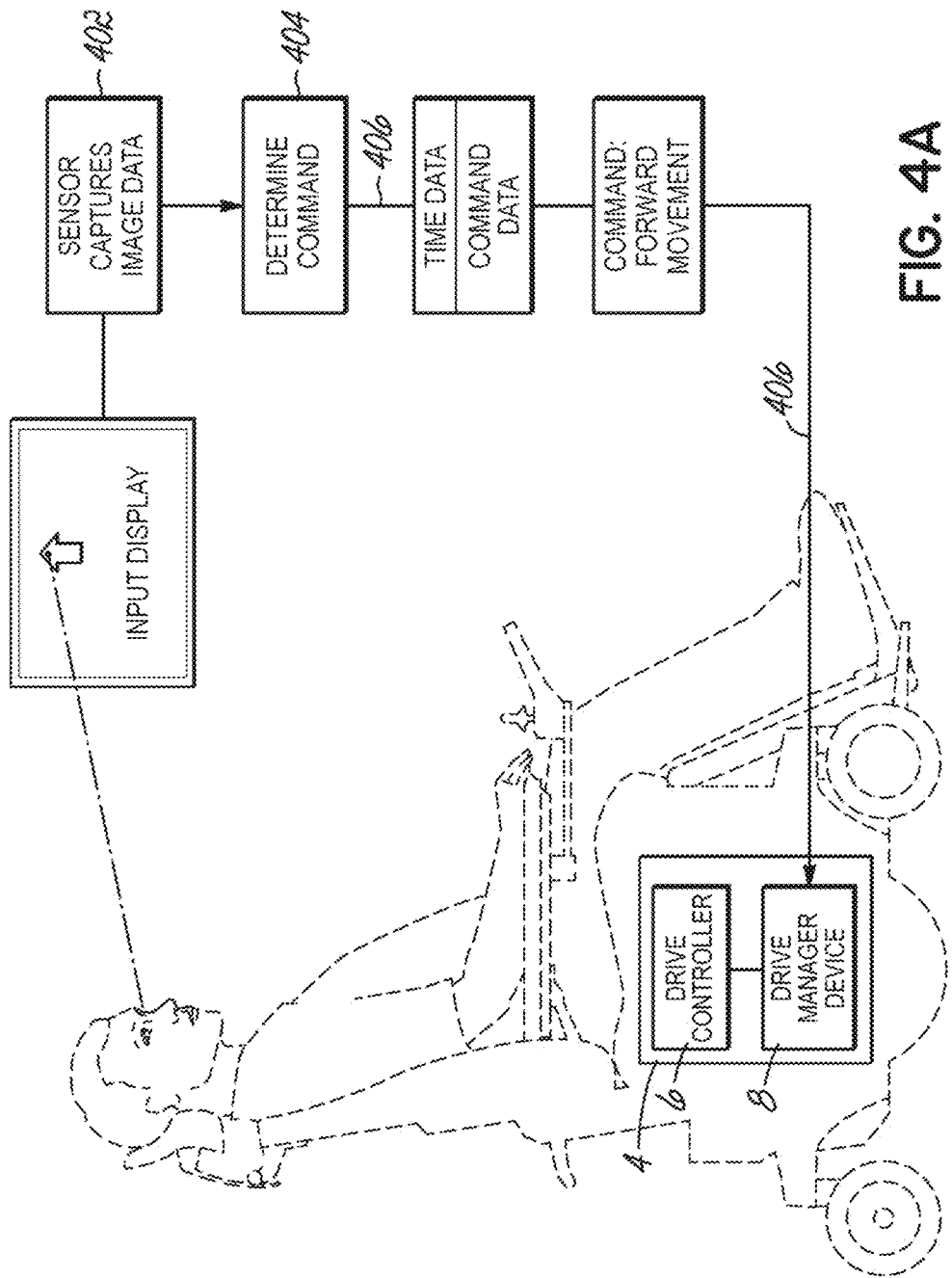

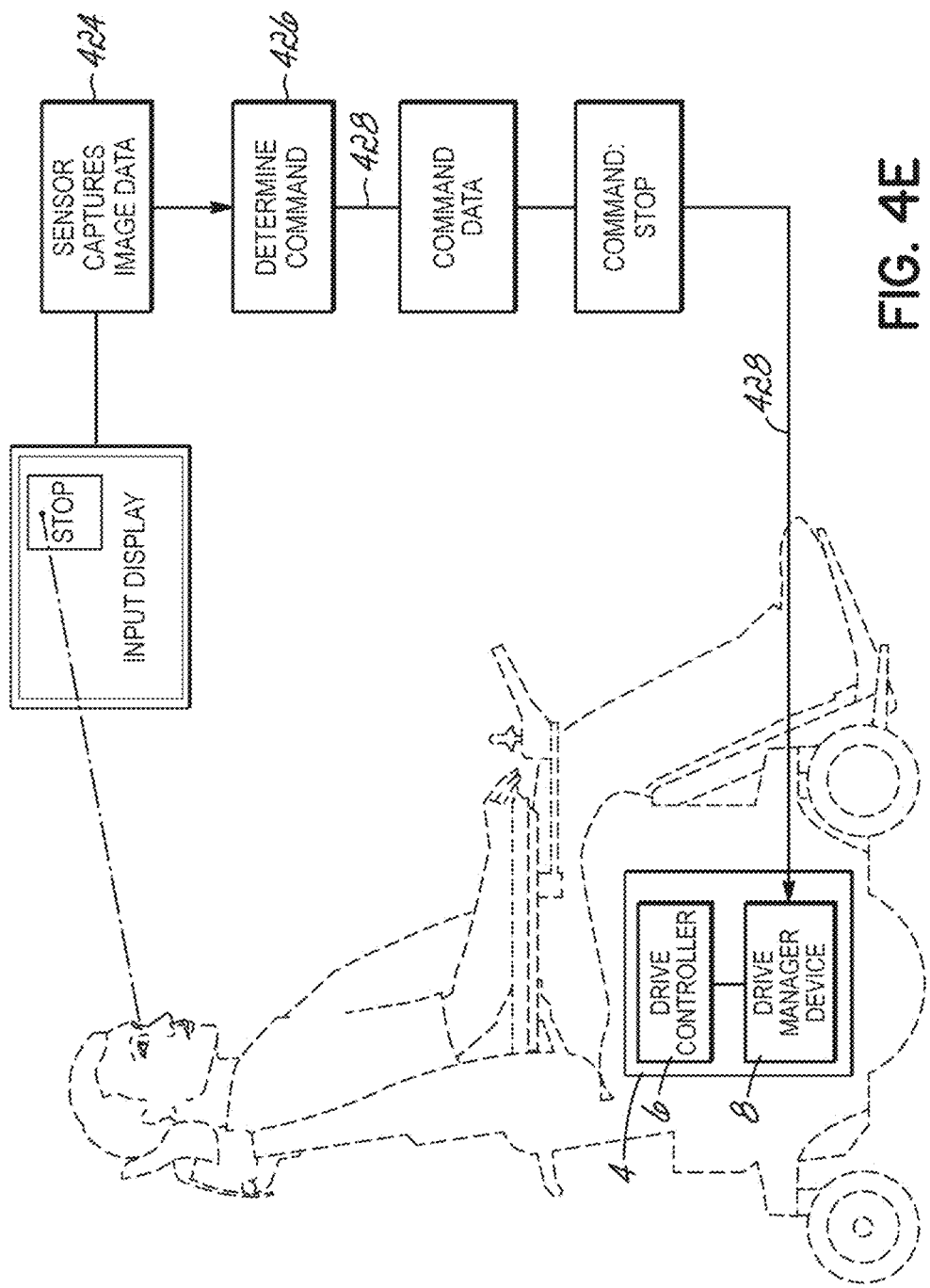

DRIVE MANAGER FOR POWER WHEELCHAIR AND RELATED METHODS

RELATED APPLICATION

This application claims priority under 35 U.S.C. § 120 and/or 35 U.S.C. § 371 to International Patent Application Serial No. PCT/US22/48190 filed Oct. 28, 2022, entitled "Drive Manager for Power Wheelchair and Related Methods," which claims priority to U.S. Provisional Patent Application Ser. No. 63/272,842, filed Oct. 28, 2021, entitled "Powered Wheelchair Alternative Drive Control Device, And Methods Of Use," which is hereby incorporated by reference, in its entirety.

FIELD OF THE INVENTION

The present invention relates generally to a device and methods for controlling a power wheelchair, and more particularly, to a device and methods which better enable a disabled individual to more readily and intuitively control the function and operation of the power wheelchair.

BACKGROUND OF THE INVENTION

It is common for a person who suffers from a progressive neurological disease, a spinal cord injury, or a traumatic brain inquiry to lose the ability to use one or more limbs. A person can lose the use of his/her limbs immediately, or in other cases, this loss may occur progressively.

A power wheelchair can significantly improve the mobility of such persons, leading to an improved overall quality of life. Typically, a power wheelchair includes a mechanical drive system operatively connected to at least the front and/or the rear wheels of the chair, a controller operatively connected to the drive system, and an input device, such as a joystick, that is operatively connected to the controller. The input device can generate and provide input commands to the controller to thereby control the mechanical drive system. U.S. Pat. No. 7,360,792, entitled "Power Wheelchair," discloses a power wheelchair and is expressly incorporated by reference herein, in its entirety.

A conventional power wheelchair can provide a patient with physical mobility, and in some situations, allows the patient to adjust the position of the seat. Seat adjustment can involve adjusting the height of the seat and the angle, or tilt, of the backrest relative to the seat. Having the ability to adjust the seating position is important because it reduces the risk of pressure injuries for the patient. Such inquiries can lead to hospitalization and/or reduced quality of life.

As stated above, a joystick is one example of an effective input device for a power wheelchair. However, for many wheelchair-bound patients, a joystick has significant limitations. For example, a patient may be unable to utilize the joystick if the patient has limited use (or no use) of their arms. The same is true if a patient becomes totally paralyzed after becoming wheelchair bound. These types of disability can seriously impair or prevent a patient from realizing the benefits associated with a power wheelchair.

Others have developed power wheelchair control systems that seek to assist the mobility of a disabled person. For example, the power wheelchair control system described in Petters son et al. U.S. Pat. No. 8,862,307 B2, entitled "Steering and Control System For A Vehicle For The Disabled," discloses a steering and control system for an electric wheelchair wherein the user may use eye control to move the wheelchair. This system also enables a staff person who is assisting the user to control the wheelchair in certain situations, via a separate joystick and a switch. Similarly, the "Ability Drive" system commercialized by Tolt Technologies, LLC offers another type of power wheelchair control system that allows a disabled person to control a power wheelchair with his or her eyes. Thus, current systems provide some benefits for a disabled or impaired patient, particularly with respect to improved mobility and independence.

Nevertheless, in one way or another each of these existing systems has one or more limitations. For example, in some situations, a disabled person (referred to hereafter as a patient) operating a power wheelchair may grow tired or need a break from controlling the power wheelchair with his or her eyes. One conventional solution allows a caregiver to operate the power wheelchair while standing behind the patient, such as by controlling a joystick positioned in the back of the power wheelchair. However, this solution caters to a more traditional patient-caregiver dynamic, and may not always provide the caregiver with the freedom of movement needed to effectively monitor the patient. For example, by walking behind the power wheelchair, the caregiver may be unable to see the facial expressions made by patient, which can make it difficult to monitor the patient's needs. Additionally, in situations where the caregiver is operating the power wheelchair with an onboard joystick, the caregiver has to walk at a speed that matches the speed of the power wheelchair, or risk losing his or her grip of the joystick.

It is an object of the present invention to overcome the limitations associated with current systems, and in particular, to do so in a manner that addresses the needs of a patient with amyotrophic lateral sclerosis ("ALS"), sometimes called Lou Gehrig's disease. ALS is a rapidly progressing neurological disease that presents significant challenges for the patient and his/her caregivers.

SUMMARY OF THE INVENTION

The one or more disclosed embodiments of the present invention represent an improvement over the prior art by allowing the patient and caregiver to seamlessly change control of a power wheelchair, while providing the caregiver the freedom of movement to walk anywhere near the power wheelchair. More particularly, according to a preferred embodiment of the present invention, the power wheelchair includes one or more moveable components, one or more motors operatively associated with the power wheelchair, a drive controller operatively connected to the one or more motors and mounted to the power wheelchair, and a drive manager device operatively connected to the drive controller. The one or more moveable components are operatively connected to the power wheelchair and include at least one of: a vertically adjustable seat, a tiltable backrest, and a plurality of wheels. The drive manager device is configured to communicate with an input collection/display unit via a first communication interface. The input collection/display unit is operable by a user in the power wheelchair. The drive manager device is configured to communicate with a caregiver unit via a second communication interface. The caregiver unit is external to the power wheelchair and operable by a caregiver. The drive manager device determines a command made by the user or the caregiver by processing command data received in a communication with the input collection/display unit or the caregiver unit, the command being associated with a request to control the power wheelchair. In response to determining the command, the drive manager device causes voltage to be applied through a third communication interface and to the drive controller, wherein the voltage causes the drive controller to interact with the one or more motors to actuate at least one of the one or more moveable components.

According to a preferred embodiment of the present invention, a drive manager device is used to manage the controls of a power wheelchair equipped with one or more motors that are capable of actuating a set of moveable components. The set of moveable components include a vertically adjustable seat, a tiltable backrest, and a plurality of wheels. The power wheelchair is further equipped with a drive controller operatively connected to the one or more motors. The drive manager device includes a set of communication interfaces, one or more memories, and one or more processors, operatively coupled to the one or more memories. The one or more processors communicate with at least one of an input collection/display unit via a first communication interface of the set of communication interfaces, and a caregiver unit via a second communication interface of the set of communication interfaces. The input collection/display unit is operable by a user in the power wheelchair. The caregiver unit is operable by a caregiver. The one or more processors determine a command made by the user or the caregiver by processing command data received in a communication with the input collection/display unit or the caregiver unit, the command being associated with a request to control the power wheelchair. In response to determining the command, the one or more processors cause voltage to be applied to the drive controller via a third communication interface of the set of communication interfaces, wherein the voltage causes the drive controller to interact with the one or more motors to actuate at least one of the set of moveable components.

According to a preferred embodiment of the present invention, a method is provided for managing the controls of a power wheelchair equipped with one or more motors, one or more moveable components, a drive controller operatively connected to the one or more motors and mounted to the power wheelchair, and a drive manager device operatively connected to the drive controller. The method includes receiving, by the drive manager device, command data associated with a command to control the power wheelchair. The command data is received from an input collection/display unit via a first communication interface or from a caregiver unit via a second communication interface. The input collection/display unit is operable by a user in the power wheelchair. The caregiver unit is operable by a caregiver. The second communication interface is preferably a wireless interface. Further, the method includes determining, by the drive manager device, the command made by the user or the caregiver by processing the received command data. Still further, the method includes causing, by the drive manager device, voltage to be applied through a third communication interface and to the drive controller, wherein the voltage causes the drive controller to interact with the one or more motors to actuate at least one of the one or more moveable components.

According to the present invention, a power wheelchair is equipped with a drive manager device and a drive controller that are configured such that control of the power wheelchair can be quickly shifted or alternated between different users. For example, the drive manager device assigns control of the power wheelchair to an input collection/display unit that is operated by a first user, such as a patient. Further, the drive manager device removes control of the power wheelchair from the input collection/display unit and assigns control of the power wheelchair to a caregiver unit that is operated by a second user, such as a caregiver. Still further, the drive manager device removes control of the power wheelchair from the caregiver unit.

According to one feature of the present invention, the drive manager device permits two devices to communicate with the power wheelchair concurrently. For example, the drive manager device permits concurrent communications with the power wheelchair, such that the input collection/display unit is able to communicate with the drive manager device over a wired communication interface (e.g., a universal serial bus (USB) interface) while the caregiver unit communicates with the drive manager device over a wireless interface (e.g., a Bluetooth Low Energy (BLE) interface).

According to another feature of the present invention, the drive manager device prevents concurrent control of the power wheelchair for safety purposes. For example, the drive manager device prevents the input collection/display unit and the caregiver unit from controlling the power wheelchair concurrently. This may be done by differentiating between communications that are made with the caregiver unit from communications made with the input collection/display unit.

By providing a flexible, seamless way to change the party controlling the power wheelchair, while preventing concurrent control, the drive manager device improves the overall safety of the patient while riding in the power wheelchair. Furthermore, by allowing the caregiver unit to communicate with the power wheelchair using a wireless interface (e.g., a Bluetooth interface), the caregiver is provided with the freedom of movement to walk anywhere in a vicinity of the power wheelchair, thereby allowing the caregiver to better monitor the patient, to engage in a conversation with the patient while walking next to him or her, and/or the like.

BRIEF DESCRIPTION OF THE DRAWINGS

FIG. 4A is a diagram that illustrates, according to the principles of the present invention, a patient using eye driving technology to request to move a power wheelchair in a forward direction.

FIG. 4E is a diagram that illustrates, according to the principles of the present invention, the patient using eye driving technology to request to stop or relinquish control of the power wheelchair.

DETAILED DESCRIPTION OF THE INVENTION

Figure 1:
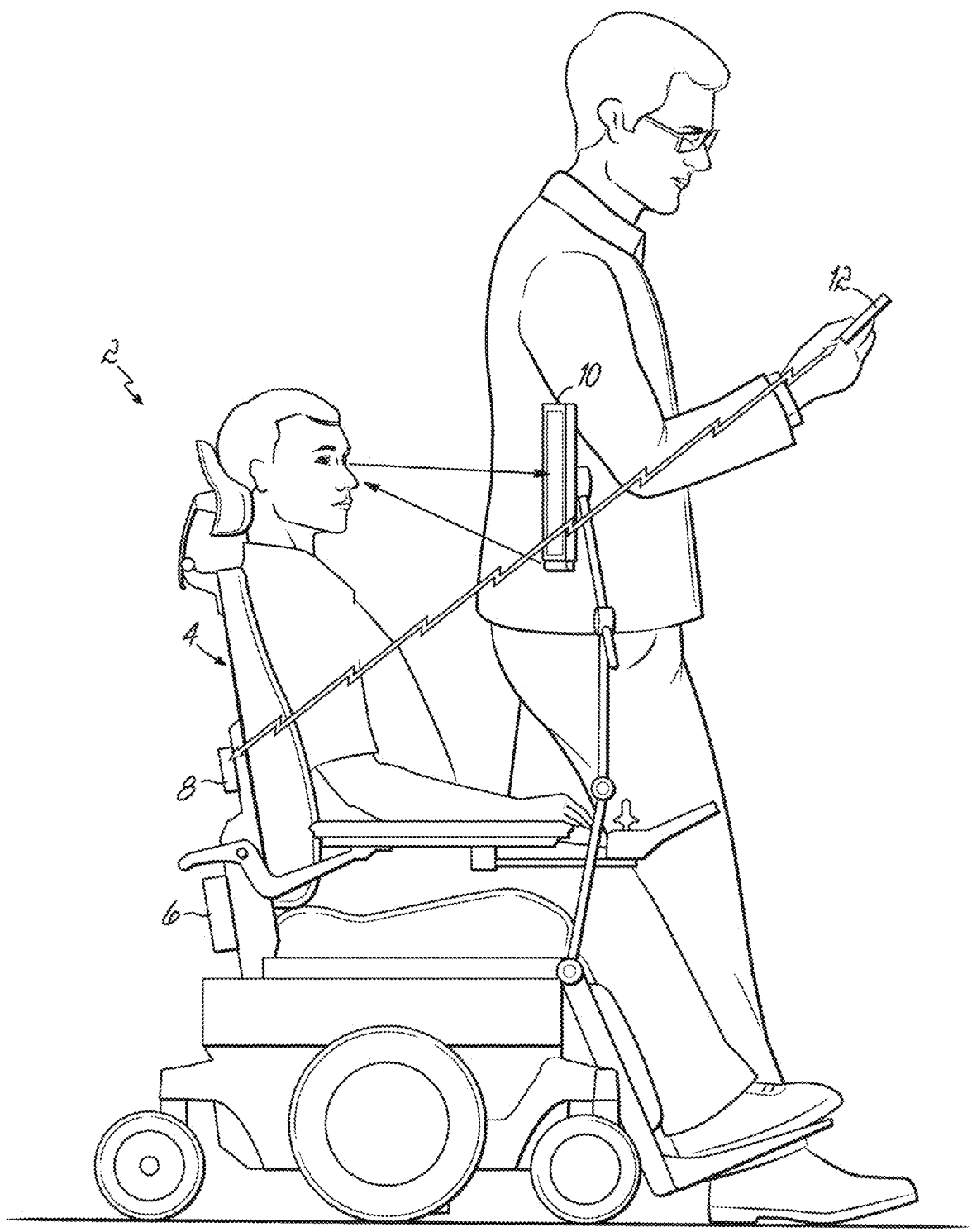
FIG. 1 is a diagram illustrating a profile view of a patient and a caregiver who are utilizing a wheelchair control assembly according to a preferred embodiment of the present invention.

FIG. 1 is a diagram illustrating a profile view of a patient and a caregiver who are utilizing a wheelchair control assembly 2 according to a preferred embodiment of the present invention. The wheelchair control assembly 2 includes a power wheelchair 4 and an input collection/display unit 10. The patient is able to use the input collection/display unit 10 to control the wheelchair using his or her eyes. The caregiver is able to control the power wheelchair 4 using a caregiver unit 12, which may be a mobile device such as a smartphone.

The power wheelchair 4 is a motorized wheelchair equipped with a drive controller 6 and a drive manager device 8. The driver controller 6 is capable of causing the wheels or seat of the power wheelchair 4 to actuate. The drive manager device 8 serves as a bridge that is able to send/receive communications to/from the input collection/display unit 10 and/or the caregiver unit 12. The drive manager device 8 is able to communicate with the drive controller 6, such that the drive manager device 8 causes the drive controller 6 to move the power wheelchair 4.

Preferably, the power wheelchair 4 has two modes of operation, a drive mode and a seat adjustment mode. The drive mode permits the patient or caregiver to drive the power wheelchair 4 and the seat adjustment mode permits the patient or caregiver to adjust a position of the seat of the power wheelchair 4. Further, the power wheelchair 4 may have one or more other modes of operation, such as a mechanical arm control mode, an autonomous drive mode, and/or another type of mode.

The patient, using his or her eyes, controls the power wheelchair 4 in the drive mode. For example, the input collection/display unit 10 may be a tablet computer mounted in front of the patient and connected to the control system of the power wheelchair 4. The input collection/display unit 10 executes a wheelchair control application that causes a user interface to be provided for display on a monitor of the tablet computer. The patient selects the drive mode by looking or gazing at a drive mode button for a threshold time period. This causes the user interface to update to display buttons depicting a set of directional arrows. The buttons depicting the set of directional arrows are, for example, directional arrows that point in directions in which the power wheelchair 4 is capable of moving.

To operate the power wheelchair 4, the patient looks or gazes at a button depicting a particular directional arrow for a threshold time period. As a result, an image capturing device, such as a camera or sensor of the input collection/display unit 10, captures image data of the patient's eyes and/or face. The input collection/display unit 10 processes the image data to identify a point of gaze of the patient (e.g., a point on the user interface in which the patient is looking or gazing). By identifying the point of gaze, the input collection/display unit 10 is able to identify the command requested by the patient (e.g., because the point of gaze corresponds to a directional arrow that is indicative of a particular command). The input collection/display unit 10 provides command data corresponding to the command to the drive manager device 8. The drive manager device 8, based on receiving the command data, causes the drive controller 6 to move the power wheelchair 4 in the requested direction.

The invention contemplates that the patient, using his or her eyes, controls the power wheelchair 4 in the seat adjustment mode. For example, the input collection/display unit 10 executes the wheelchair control application which causes a user interface to be provided for display on the monitor of the tablet computer. The patient selects the seat adjustment mode by looking or gazing at a seat adjustment mode button for a threshold time period. This causes the user interface to update to display buttons that depict seat adjustment settings. The display buttons depicting seat adjustment settings are, for example directional arrows that point in directions in which the seat is capable of moving, a scale depicting a set of fixed positions in which the seat is capable of moving, and/or another type of display button.

To adjust the seat of the power wheelchair 4, the patient looks or gazes at a button depicting a particular seat adjustment setting for a threshold time period. As a result, the image capturing device captures image data of the patient's eyes and/or face. The input collection/display unit 10 processes the image data to identify a point of gaze of the patient. By identifying the point of gaze, the input collection/display unit 10 is able to identify the command requested by the patient (e.g., because the point of gaze corresponds to a directional arrow that is indicative of a command to move the seat of the power wheelchair 4 into a particular position). The input collection/display unit 10 provides command data corresponding to the command to the drive manager device 8. The drive manager device 8 causes the drive controller 6 to move the seat of the power wheelchair 4 into the requested position.

Further, the caregiver, using the caregiver unit 12, controls the power wheelchair 4 in the drive mode. For example, the caregiver unit 12 executes the wheelchair control application to cause a user interface to be provided for display. The caregiver selects the drive mode by touching or pressing a drive mode button, which causes the user interface to update to display a virtual joystick.

To operate the power wheelchair 4, the caregiver touches or presses on the virtual joystick, so as to move the virtual joystick in a particular direction. When the caregiver moves the virtual joystick in a particular direction, the caregiver unit 12 generates command data corresponding to the particular direction. The caregiver unit 12 provides the command data to the drive manager device 8, and the drive manager device 8 causes the drive controller 6 to move the power wheelchair 4 in the particular direction.

The caregiver, using the caregiver unit 12, controls the power wheelchair 4 in the seat adjustment mode. For example, the caregiver unit 12 executes the wheelchair control application to cause a user interface to be provided for display. The caregiver selects the seat adjustment mode by touching or pressing a seat adjustment mode button, which causes the user interface to update to display a virtual joystick.

To adjust the seat of the power wheelchair 4, the caregiver touches or presses on the virtual joystick, so as to move the virtual joystick in a particular direction. When the caregiver moves the virtual joystick in a particular direction, the caregiver unit 12 generates command data corresponding to the particular direction. The caregiver unit 12 provides the command data to the drive manager device 8. The drive manager device 8, based on receiving the command data, causes the drive controller 6 to move the seat of the power wheelchair 4 into the requested position.

According to one aspect of the invention, the drive manager device 8 removes control of the power wheelchair 4 from the input collection/display unit 10 and assigns control of the power wheelchair 4 to the caregiver unit 12. For example, assume the patient is controlling the power wheelchair 4 with his or eyes, but that the patient no longer wishes to control the power wheelchair 4. In this case, the patient looks or gazes at a button depicting a stop button for a threshold time period. As a result, the image capturing device captures image data of the patient's eyes and/or face. The input collection/display unit 10 processes the image data to identify the point of gaze of the patient. By identifying the point of gaze, the input collection/display unit 10 is able to identify the stop command requested by the patient and to provide stop command data to the drive manager device 8. The drive manager device 8, based on receiving the stop command data, causes the drive controller 6 to stop the power wheelchair 4 such that the patient is no longer able to control the power wheelchair 4 using his or her eyes.

Continuing with the example, the caregiver unit 12 establishes a communication session, such as a Bluetooth communication session, with the drive manager device 8. This allows the caregiver unit 12 to operate the drive mode of the power wheelchair 4 and to send, to the drive manager device 8, command data indicating to move the power wheelchair 4 in a given direction. Next, the drive manager device 8, based on receiving the command data, causes the drive controller 6 to move the power wheelchair 4 in the given direction.

According to one aspect of the invention, the drive manager device 8 removes control of the power wheelchair 4 from the caregiver unit 12 and assigns control of the power wheelchair 4 to the input collection/display unit 10. For example, assume the caregiver is controlling the power wheelchair 4 using a virtual joystick displayed on a user interface of the caregiver unit 12. If the caregiver wants to stop controlling the power wheelchair 4, the caregiver selects a stop button on the user interface, causing stop command data to be provided to the drive manager device 8. The drive manager device, based on receiving the stop command data, causes the driver controller 6 to stop the power wheelchair 4 such that caregiver is no longer able to control the power wheelchair 4.

Continuing with the example, the patient interacts with a user interface displayed on the input collection/display unit 10 to submit a request to control the power wheelchair 4. For example, the patient looks or gazes at a start button for a threshold time period. As a result, the image capturing device captures image data of the patient's eyes and/or face. The input collection/display unit 10 processes the image data to identify a start button as the point of gaze of the patient. The input collection/display unit 10 provides start command data to the drive manager device 8. The drive manager device 8, based on receiving the start command data, assigns control of the power wheelchair 4 to the input collection/display unit 10.

As described above, control of the power wheelchair 4 is removed because a user has willingly relinquished his or her control. In some embodiments, a user can be forced to relinquish or pause his or her control as a safety precaution. For example, assume the patient is driving the power wheelchair 4 using the input collection/display unit 10, where the input collection/display unit 10 communicates with the drive manager device 8 using a first communication interface (e.g., a USB interface). The caregiver unit 12 is connected to the drive manager device 8 at the same time using a second communication interface (e.g., a Bluetooth interface). To prevent concurrent control of the power wheelchair 4, the drive manager device 8 prevents drive controls (e.g., the virtual joystick) from appearing on the user interface of the caregiver unit 12. However, the user interface displays a stop button and/or a pause button, such that the caregiver is able to pause or stop the power wheelchair 4 in the event of an emergency. This occurs despite that control of the power wheelchair 4 has been assigned to the input collection/display unit 10.

In this way, the drive manager device 8 allows control of the power wheelchair 4 to seamlessly alternate between patient and caregiver, while providing the caregiver the freedom of movement to walk anywhere in a vicinity of the power wheelchair 4. Furthermore, by preventing concurrent control of the power wheelchair 4, and by permitting control override features for emergencies, the drive manager device 8 improves the overall safety of the power wheelchair 4.

Figure 2:
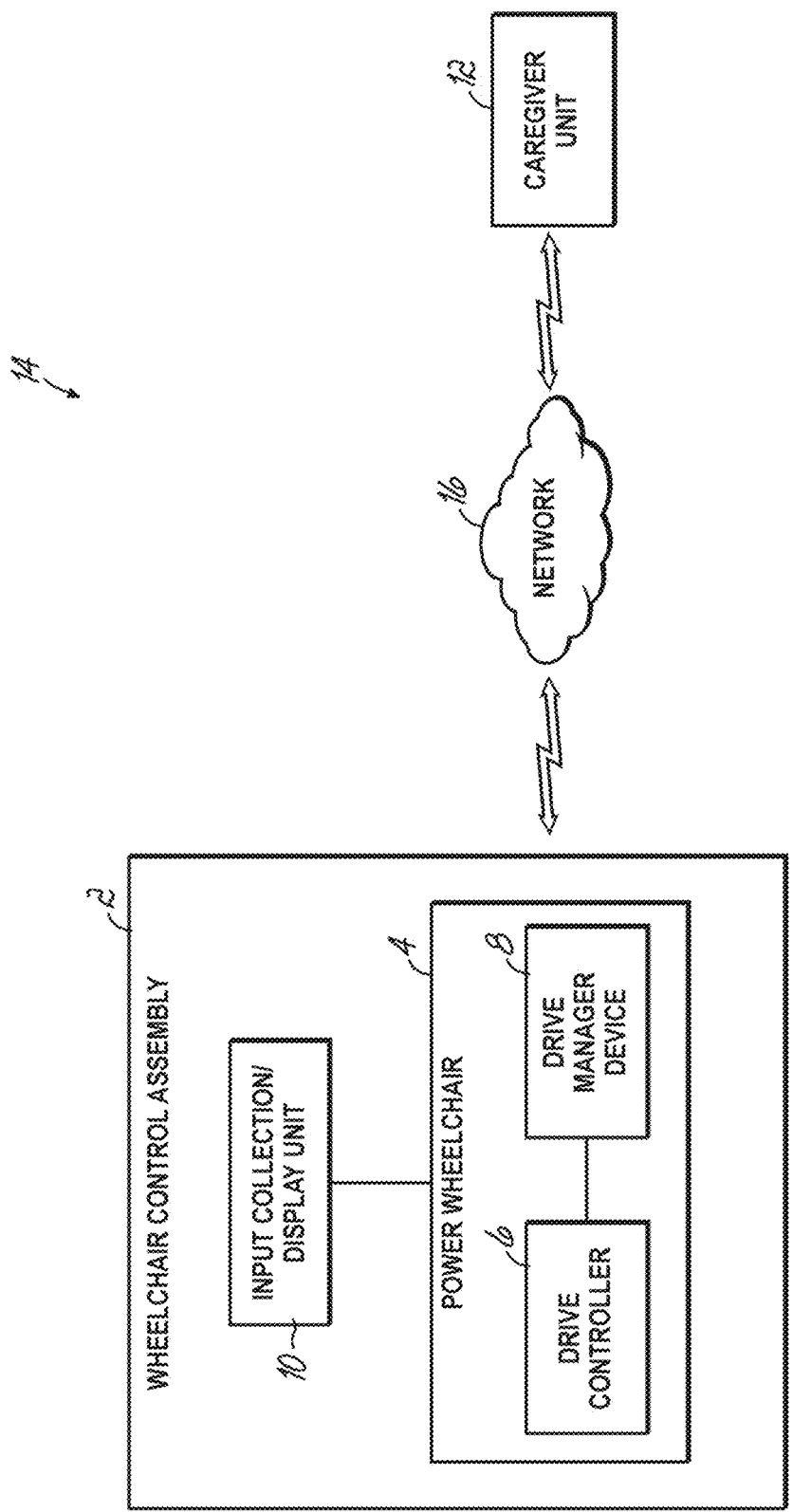
FIG. 2 is a diagram of an example environment in which systems and/or methods described herein may be implemented, according to the present invention.

FIG. 2 is a diagram of an example environment 14 in which systems and/or methods described herein may be implemented. As shown in FIG. 2, the example environment 14 includes a power wheelchair assembly 2 that communicates with a caregiver unit 12 over a network 16. Devices of environment 14 may interconnect via wired connections, wireless connections, or a combination of wired and wireless connections.

The power wheelchair assembly 2 includes a power wheelchair 4 and an input collection/display unit 10. The power wheelchair 4 includes wheels, a seat, leg rests, foot plates, arm rests, one or more motors, a drive controller 6, a drive manager device 8, and/or the like.

The wheels are used to move the power wheelchair 4 in a given direction. In some embodiments, the wheels are turned or actuated using the one or more motors. In some embodiments, the seat is a vertically adjustable seat with a tiltable backrest. To adjust the seat, the one or more motors, or a mechanical component capable of causing an actuation of the seat, causes the seat to actuate such that a position of the vertically adjustable seat and/or the tiltable backrest are adjusted.

The leg rests and foot plates provide a patient with a place to rest his or her legs and feet. The arm rests provide a patient with a place to rest his or her arms. In some embodiments, a position of the leg rests, foot plates, and/or arm rests are adjustable. For example, the one or more motors, or a mechanical component capable of causing an actuation of the leg rests, foot plates, and/or arm rests, causes a leg rest, foot plate, and/or arm rest to actuate, such that a position of the leg rest, foot plate, and/or arm rest is adjusted.

The one or more motors are used to move or actuate components of the power wheelchair 4, such as by moving or actuating the wheels, seat, leg rests, foot rests, arm rest, and/or the like. The one or more motors include an electric motor, a brush motor, a brushless motor, and/or another type of motor. In some embodiments, the one or more motors include a first motor capable of actuating a first wheel of the power wheelchair 4 and a second motor capable of actuating a second wheel of the power wheelchair 4. In some embodiments, the same motor actuates multiple wheels of the power wheelchair 4.

One or more mechanical actuation components may be implemented in place of (or in addition to) the one or more motors. In some embodiments, the one or more motors or the one or more mechanical actuation components actuate other types of components or devices that are mountable or attachable to the power wheelchair 4. For example, the one or more motors or the one or more mechanical actuation components may actuate a robotic arm used to help a patient grab onto nearby objects while operating the power wheelchair 4.

The drive controller 6 includes one or more devices or components capable of receiving, storing, processing, and/or transmitting information associated with the control of the power wheelchair 4. For example, the drive controller 6 includes an electrical circuit or circuit board, such as a printed circuit board (PCB), that is used to connect components of the drive controller 6 (e.g., such as a processor, a memory, and/or any other components described in connection with FIG. 3). The drive controller 6 is configured to cause the wheels, seat, arm rests, and/or leg rests of the power wheelchair 4 to actuate. For example, the drive controller 6 interacts with the one or more motors to cause the wheels to actuate in a given direction. To provide another example, the drive controller 6 interacts with the one or more motors or one or more other mechanical actuation components to cause the seat, arm rests, and/or leg rests to actuate, such that a position of the seat, arm rests, and/or leg rests is adjusted.

The drive controller 6 includes an alternative drive control interface used to communicate with the drive manager device 8. For example, the alternative drive control interface provides a first connection to the drive manager device 8 by connecting to a first communication interface, such as a power toggle interface (e.g., a 3.5 mm interface), and provides a second connection to the drive manager device 8 by connecting to a second communication interface, such as a 9-pin interface. By using the alternative drive control interface, requests to power on the power wheelchair 4 can be provided via the first connection (e.g., between the power toggle interface and the alternative drive control interface) while requests to control the power wheelchair 4 can be provided via the second connection (e.g., between the 9-pin interface and alternative drive control interface).

The drive manager device 8 includes one or more devices or components capable of receiving, storing, processing, and/or transmitting information associated with the control of the power wheelchair 4. For example, the drive manager device 8 includes an electrical circuit or circuit board, such as a PCB, that is used to connect components of the drive manager device 8 (e.g., such as a processor, a memory, and/or any other components described in connection with FIG. 3).

The drive manager device 8 communicates with the input collection/display unit 10. For example, the drive manager device 8 communicates with the input collection/display unit 10 using a communication interface. In some embodiments, the communication interface may be a wired interface, such as a universal serial bus (USB) interface or other type of wired interface. In some embodiments, the communication interface may be a wireless interface, such as a Bluetooth interface, Bluetooth Low Energy (BLE) interface, or other type of wireless interface.

The drive manager device 8 communicated with the caregiver unit 12. For example, the drive manager device 8 communicates with the caregiver unit 12 using a communication interface. In some embodiments, the communication interface may be a wireless interface, such as a Bluetooth interface or BLE interface. To communicate over the Bluetooth interface, the caregiver unit 12 registers, pairs, and/or synchronizes with the driver manager device 8. For example, the caregiver unit 12 performs a Bluetooth scan or BLE scan to establish a communication session with the drive manager device 8. In some embodiments, the communication interface may a wired interface, such as a USB interface.

The drive manager device 8 communicates with the drive controller 6 using one or more of multiple communication interfaces. For example, the drive manager device 8 communicates with the driver controller 6 using a power toggle interface (e.g., a 3.5 mm interface), a 9-pin interface, and/or another type of interface. The power toggle interface is used for communications associated with turning the power wheelchair 4 on or off. The 9-pin interface is used for communications associated with driving the power wheelchair 4 and/or communications associated with adjusting a position of the seat, arm rests, and/or leg rests of the power wheelchair 4.

Input collection/display unit 10 includes one or more devices capable of receiving, storing, capturing, processing, and/or transmitting information associated with controlling the power wheelchair 4. The input collection/display unit 10 includes an image capturing device, a tablet computer, laptop computer, mobile device, desktop computer, a combination these devices, a combination of these devices, and/or a similar type of device. In some embodiments, input collection/display unit 10 is a tablet computer mounted in front of the occupant of the power wheelchair 4. In some embodiments, the input collection/display unit 10 is connected to a control system of the power wheelchair 4. In some embodiments, the input collection/display unit 10 includes an image capturing device configured to obtain image data depicting the eyes and/or face of the occupant of the power wheelchair 4. The image capturing device includes a sensor, a camera (e.g., a smart camera, an RGB digital camera, an infrared (IR) camera, etc.), a light emitter, a dedicated coprocessor (e.g., such as an image or geometric co-processor), a combination of these devices, and/or a similar type of device. The input collection/display unit 10 supports a wheelchair control application. The wheelchair control application includes one or more user interfaces that permit a patient to use the input collection/display unit 10 to control the power wheelchair 4.

Caregiver unit 12 includes one or more devices capable of receiving, storing, capturing, processing, and/or transmitting information associated with the control of the power wheelchair 4. For example, the caregiver unit 12 includes a wireless communication device, a smartphone, a radiotelephone, a personal communications system (PCS) (e.g., that may combine a cellular radiotelephone with data processing and data communications capabilities), a laptop computer, a tablet computer, a personal gaming system, an internet of things (IoT) device, a combination of these devices, and/or a similar type of device. In some embodiments, the caregiver unit 12 supports a wheelchair control application. The wheelchair control application includes one or more user interfaces that permit a caregiver to gain remote control the power wheelchair 4.

Network 16 includes one or more wired and/or wireless networks. For example, the network 16 includes a cellular network (e.g., a 5G network, a 4G network, such as an LTE network, a 3G network, etc.), a wireless local area network, a local area network (LAN), a public land mobile network (PLMN), a wide area network (WAN), a wireless personal area network (WPAN), a telephone network, an intranet, the Internet, a fiber optic-based network, a cloud computing network, and/or a combination of these or other types of networks.

The number and arrangement of devices and networks shown in FIG. 2 are provided as one or more examples. In practice, there may be additional devices and/or networks, fewer devices and/or networks, different devices and/or networks, or differently arranged devices and/or networks than those shown in FIG. 2. Furthermore, two or more devices shown in FIG. 2 may be implemented within a single device, or a single device shown in FIG. 2 may be implemented as multiple, distributed devices. Additionally, or alternatively, a set of devices (e.g., one or more devices) of environment 14 may perform one or more functions described as being performed by another set of devices of environment 14.

Figure 3:
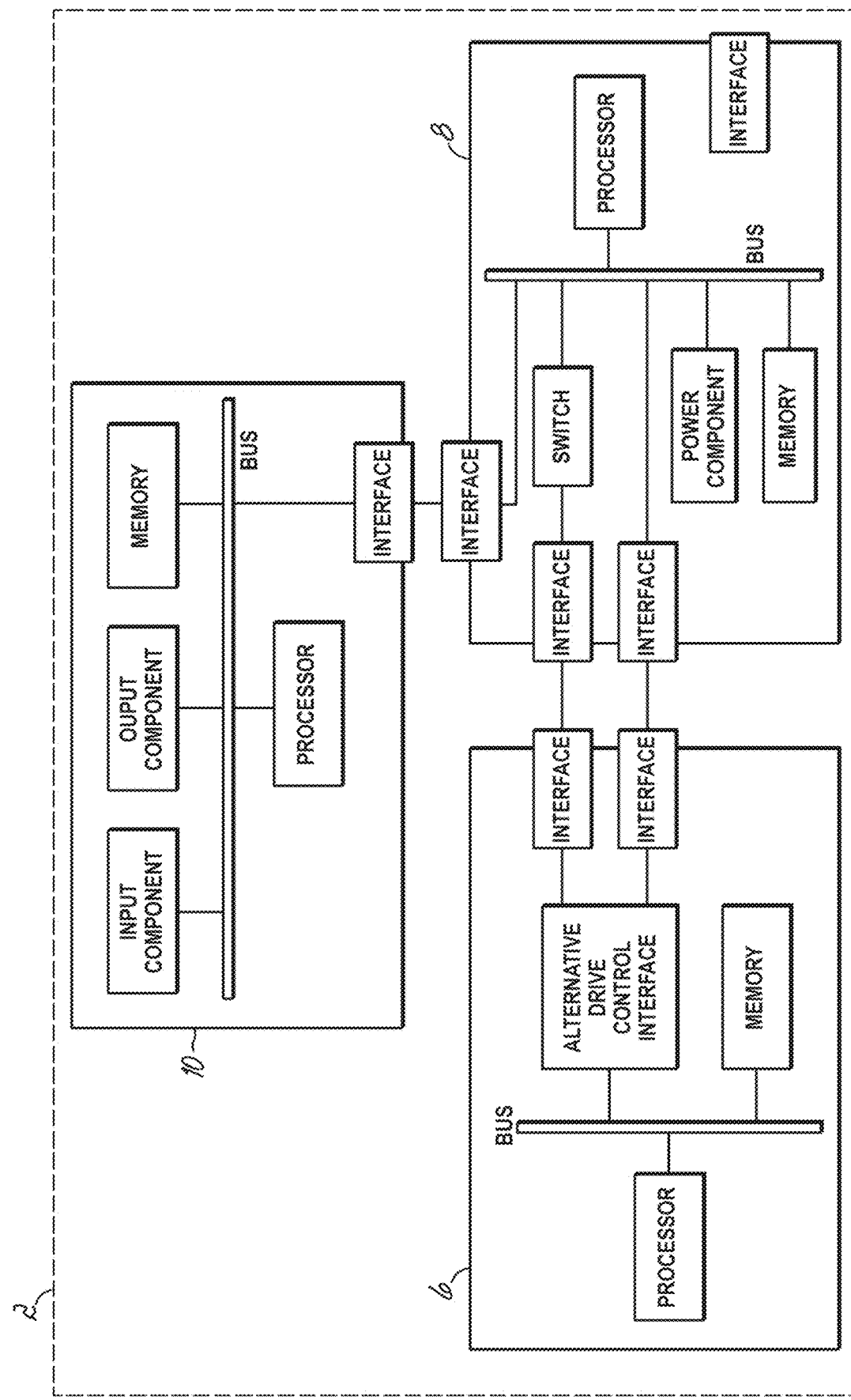
FIG. 3 is a diagram that schematically shows exemplary components of one or more devices of the power wheelchair assembly of FIG. 2.

FIG. 3 is a diagram of example components of one or more devices of the power wheelchair assembly 2 of FIG. 2. As shown in FIG. 3, one or more devices of the power wheelchair assembly 2 (e.g., the drive controller 6, the drive manager device 8, and/or the input collection/display unit 10) each include a bus, a processor, a memory, and one or more interfaces.

A bus permits communication among one or more components within a device and/or permits communication among one or more components between devices. A processor is implemented in hardware, firmware, and/or a combination of hardware and software. As used herein, the term "processor" refers to one or more processors capable of being programmed to perform a function. The processor includes a central processing unit (CPU), a graphics processing unit (GPU), an accelerated processing unit (APU), a microprocessor, a microcontroller, a digital signal processor (DSP), a field-programmable gate array (FPGA), an application-specific integrated circuit (ASIC), a combination of processing components, and/or another type of processing component. In a preferred embodiment, the processor of the drive manager device 8 is a microcontroller. The memory includes a random access memory (RAM), a read only memory (ROM), and/or another type of dynamic or static storage device (e.g., a flash memory, a magnetic memory, and/or an optical memory) that stores information and/or instructions for use by the processor.

The drive controller 6 includes an alternative drive control interface. The alternative drive control interface connects to interfaces of the drive manager device 8. For example, the alternative drive control interface connects to a power toggle interface (e.g., a 3.5 mm interface) of the drive manager device 8 and connects to a 9-pin interface of the drive manager device 8.

The drive manager device 8 includes a set of interfaces. The set of interfaces include the power toggle interface (e.g., 3.5 mm interface), the 9-pin interface, a communication interface used to communicate with the input collection/display unit 10, such as a USB interface, and a communication interface used to communicate with the caregiver unit 12, such as a Bluetooth or BLE interface. Communications made over the USB and Bluetooth interface can be made using a serial communication protocol or similar type of protocol. In some embodiments, the drive manger device 8 may include one or more other interfaces, such as a serial wire debug (SWD) interface, a micro-USB interface, and/or a similar type of interface.

The drive manager device 8 includes a power component. The power component includes a power source, a voltage regulator, and/or any other component capable of providing, manipulating, distributing, and/or transmitting electrical current. In some embodiments, the voltage regulator takes input power from the USB interface and distributes the input power to one or more other components.

The drive manager device 8 includes a switch. The switch is a contact closure style switch, a switch connectable to a 3.5 mm interface, and/or another type of switch. In some embodiments, the switch is a contact closure style switch that connects to the power toggle interface. The power toggle interface may, for example, be a 3.5 mm interface, such as a 3.5 mm interface with a mono style tip and sleeve connection. In some embodiments, the switch connecting to the 3.5 mm interface provides a contact-closure-switch-style behavior that allows the power of the power wheelchair 4 to be toggled on and off. The switch includes a transistor that closes a circuit connection by connecting the tip and sleeve of the 3.5 mm interface. The transistor is controlled, for example, by a processor such as a microcontroller. The processor controls the transistor by causing digital voltage to be applied when the processor receives command data indicating a command being requested by a user (e.g., such as a command requesting to turn the power wheelchair 4 on or off, or another type of command).

The drive manager device 8 includes a 9-pin interface. In some embodiments, the 9-pin interface is configured such that different commands are reserved for different pins and/or different combinations of pins. For example, a 9-pin interface includes five action pins, including a pin corresponding to a movement in a forward direction, a pin corresponding to a movement in a backward direction, a pin corresponding to a movement in a left direction, a pin corresponding to a movement in a right direction, and a pin corresponding to changing the mode of operation. A sixth pin is used as a ground pin. The remaining pins are, for example, used to send/receive voltage from the power wheelchair 4, be used for a device detection method, and/or be used for any other reason known in the art. Multi-directional commands (e.g., forward and left, forward and right, etc.) can be signaled in combination (e.g., by causing voltage to be applied to multiple pins).

To trigger execution of a command to control the power wheelchair 4, a configurable quantity of voltage is applied to one or more pins of the 9-pin interface. In some embodiments, such as in digital operation, the pins are signaled as active using a first voltage threshold and signaled as inactive using a second voltage threshold. For example, a pin is signaled as active if an applied voltage satisfies (e.g., is less than or equal to) a first voltage threshold of 0.7 volts, and a pin is signaled as inactive if an applied voltage satisfies (e.g., is greater than or equal to) a second voltage threshold of 1.4 volts. In some embodiments, a pin is signaled as active if an applied voltage is 0 volts. In some embodiments, a pin is signaled as active if an applied voltage is any quantity of voltage greater than 0 volts. In some embodiments, such as in analog operation, applied voltage values have ranges spanning from negative voltage values to positive voltage values.

The driver manager device 8 includes one or more other components. For example, the drive manager device 8 includes one or more decoupling capacitors, one or more indicator light-emitting diodes (LEDs), and/or the like.

The input collection/display unit 10 uses the USB interface to communicate with the drive manager device 8. In some embodiments, the input collection/display unit 10 utilizes one or more other communication interfaces described herein.

The input collection/display unit 10 includes an input component. The input component permits one or more of the devices of the power wheelchair assembly 2 to receive information, such as via user input (e.g., a touch screen display, a keyboard, a keypad, a mouse, a button, a switch, and/or a microphone). Additionally, or alternatively, the input component includes a component for determining a location (e.g., a global positioning system (GPS) component). Additionally, or alternatively, the input component includes an image capturing device, an accelerometer, a gyroscope, an actuator, another type of positional or environmental sensor, and/or the like. The image capturing device includes a sensor, a camera (e.g., a smart camera, an RGB digital camera, an infrared (IR) camera, etc.), a light emitter, a dedicated coprocessor (e.g., such as an image or geometric co-processor), a combination of these devices, and/or a similar type of device.

The input collection/display unit 10 includes an output component. The output component provides output information using, e.g., a display, a speaker, a haptic feedback component, an audio or visual indicator, and/or the like.

The number and arrangement of components shown in FIG. 3 are provided as an example. In practice, the wheelchair control assembly 2 may include additional components, fewer components, different components, or differently arranged components than those shown in FIG. 3. Additionally, or alternatively, a set of components (e.g., one or more components) of the wheelchair control assembly 2 may perform one or more functions described as being performed by another set of components of the wheelchair control assembly 2.

FIGS. 4A-4H illustrate one or more ways in which control of the power wheelchair 4 can shift or alternate between a patient and a caregiver. As a preliminary matter, the patient can interact with a user interface of an input collection/display unit 10 in order to power on the power wheelchair 4. For example, the patient gazes or looks at a power button displayed as part of a home screen of the wheelchair control application. As a result, a sensor of the input collection/display unit 10 captures image data of the patient's eyes and/or face. The input collection/display unit 10 processes the image data to identify a point of gaze of the patient. The point of gaze of the patient indicates that the patient's gaze is directed toward the power button on a user interface of the wheelchair control application. This causes the input collection/display unit 10 to generate power command data and to provide the power command data to the drive manager device 8. The power command data is provided over a communication interface, such as a universal serial bus (USB) interface.

Continuing with the example, the drive manager device 8, based on receiving the power command data, causes power to be applied to one or more other components of the power wheelchair 4. For example, the drive manager device 8 causes voltage to be applied to the drive controller 6 using another communication interface, such as a power toggle interface (e.g., a 3.5 mm interface). In this way, the patient uses the input collection/display unit 10 to toggle on the power of the power wheelchair 4.

FIG. 4A is a diagram that illustrates, according to the principles of the present invention, the patient using eye driving technology to request to move the power wheelchair 4 in a forward direction. For example, the patient, while seated in the power wheelchair 4, interacts with a user interface of the input collection/display unit 10 to request to control the power wheelchair 4. The user interface displays a menu of commands that are part of a wheelchair control application. The menu of commands includes, for example, a command to drive the power wheelchair 4, a command to adjust a positioning of the seat of the power wheelchair 4, and/or the like.

To start a drive mode of the power wheelchair 4, the patient gazes or looks at a drive mode display button on the user interface and the drive mode is selected by having the patient continue to gaze or look at the button for a threshold time period. While the patient is gazing or looking at the drive mode display button, the sensor of the image collection/display unit 10 captures image data of the patient's eyes and/or face. The image collection/display unit 10 processes the image data to identify a point of gaze of the patient (e.g., which may indicate that the patient is gazing at the drive mode display button). Next, the image collection/display unit 10 generates command data requesting to enter the drive mode and may provide the command data to the drive manager device 8. The drive manager device 8 verifies that the power wheelchair 4 is not currently being controlled by another user and grants the input collection/display unit 10 control of the power wheelchair 4. This causes the user interface of the input collection/display unit 10 to update and display a drive mode home screen.

To begin driving the power wheelchair 4, the patient looks at a start button displayed on the drive mode home screen for a threshold time period. While the patient is gazing or looking at the start button, the sensor of the image collection/display unit 10 captures image data of the patient's eyes and/or face. The image collection/display unit 10 processes the image data to identify a point of gaze of the patient (e.g., which may indicate that the patient is gazing at the start button). Next, the image collection/display unit 10 generates start command data and provides the start command data to the drive manager device 8. Once the drive manager device 8 has started the drive mode, the user interface of the input collection/display unit 10 updates to display a set of directional arrows. The set of directional arrows are used to move the power wheelchair 4 in a number of different directions, including forward, reverse, left, right, forward and left, forward and right, reverse and left, reverse and right, nudge left, and nudge right.

As shown by reference number 402, the sensor of the input collection/display unit 10 captures image data of the patient's eyes and/or face. For example, to request to move the power wheelchair 4 in a forward direction, the patient gazes or looks at a button of a forward directional arrow that is displayed on the user interface of the wheelchair control application. While the patient is looking at the forward directional arrow, the sensor captures image data of the patient's eyes and/or face. The sensor is configured to continuously capture image data based on a trigger, such as the patient selecting the drive mode, the power wheelchair 4 being powered on, the wheelchair control application launching, and/or another type of trigger. While one or more embodiments described herein refer to image data as being captured over time, it is to be understood that the data captured may be image data, video data, sound data, and/or a combination thereof.

As shown by reference number 404, the input collection/display unit 10 processes the image data to determine the command issued by the patient. For example, the input collection/display unit 10 processes the image data to identify a point of gaze of the patient or a motion of the patient's eye relative to his or her head. To identify the point of gaze or motion of the patient's eye relative to his or her head, the input collection/display unit 10 executes an image processing technique, an eye tracking technique, a polynomial transformation technique, an image smoothing and/or noise reduction technique, a natural language processing technique, and/or any other technique known in the art.

To provide a specific example, an eye tracking technique and/or a polynomial transformation technique is executed to compute vectors for gaze direction and head orientation. These vectors are used to project the gaze of the patient's eyes onto a plane that corresponds to the directional arrows displayed on the user interface. The plane is an XY coordinate grid used to map particular pixels to particular directional arrows. The input collection/display unit 10 then uses the computed vectors to determine that the gaze of the patient's eyes corresponds to the forward directional arrow shown on the user interface. In some embodiments, the input collection/display unit 10 further verifies that the patient has been looking at the forward directional arrow for a threshold time period.

Once the patient's gaze has been identified as corresponding to the forward directional arrow for the threshold time period, the input collection/display unit 10 determines that the command issued by the patient is a command to move in a forward direction. For example, the input collection/display unit 10 has access to a data structure that associates positions of directional arrows within the XY coordinate grid with command data specifying particular commands. Thus, the input collection/display unit 10 compares coordinates corresponding to the gaze of the patient with the data structure that associates stored coordinates with particular directional commands. In this example, the input collection/display unit 10 determines that the coordinates corresponding to the gaze of the patient matches stored coordinates corresponding to a command to move in a forward direction. This allows the input collection/display unit 10 generate or reference command data indicating to move in the forward direction (referred to hereafter as forward command data).

In some embodiments, the input collection/display unit 10 determines a duration during which the power wheelchair 4 is to move in the specified direction. For example, the input collection/display unit 10 has access to a data structure that associates command data with stored time data. In this case, the input collection/display unit 10, after determining the command made by the patient, references the data structure to identify time data that has been stored in association with command data of the command made by the patient. In the example shown, the data structure associates forward command data with time data that indicates a duration during which the power wheelchair 4 is to move in the forward direction.

In some embodiments, the patient is required to continue to look at the forward directional arrow in order for the power wheelchair 4 to continue to move in the forward direction. For example, the power wheelchair 4 moves in the forward direction while the patient continues to gaze at the forward directional arrow. However, when the patient's gaze is directed away from the forward directional arrow, the power wheelchair 4 stops moving in the forward direction.

As shown by reference number 406, the input collection/display unit 10 provides the forward command data and the time data to the drive manager device 8. For example, the input collection/display unit 10 uses a communication interface, such as a USB interface, to provide the forward command data and/or the time data to the drive manager device 8.

In this way, the patient uses his or her eyes to input a request to move the power wheelchair 4 in a forward direction.

Figure 4B:
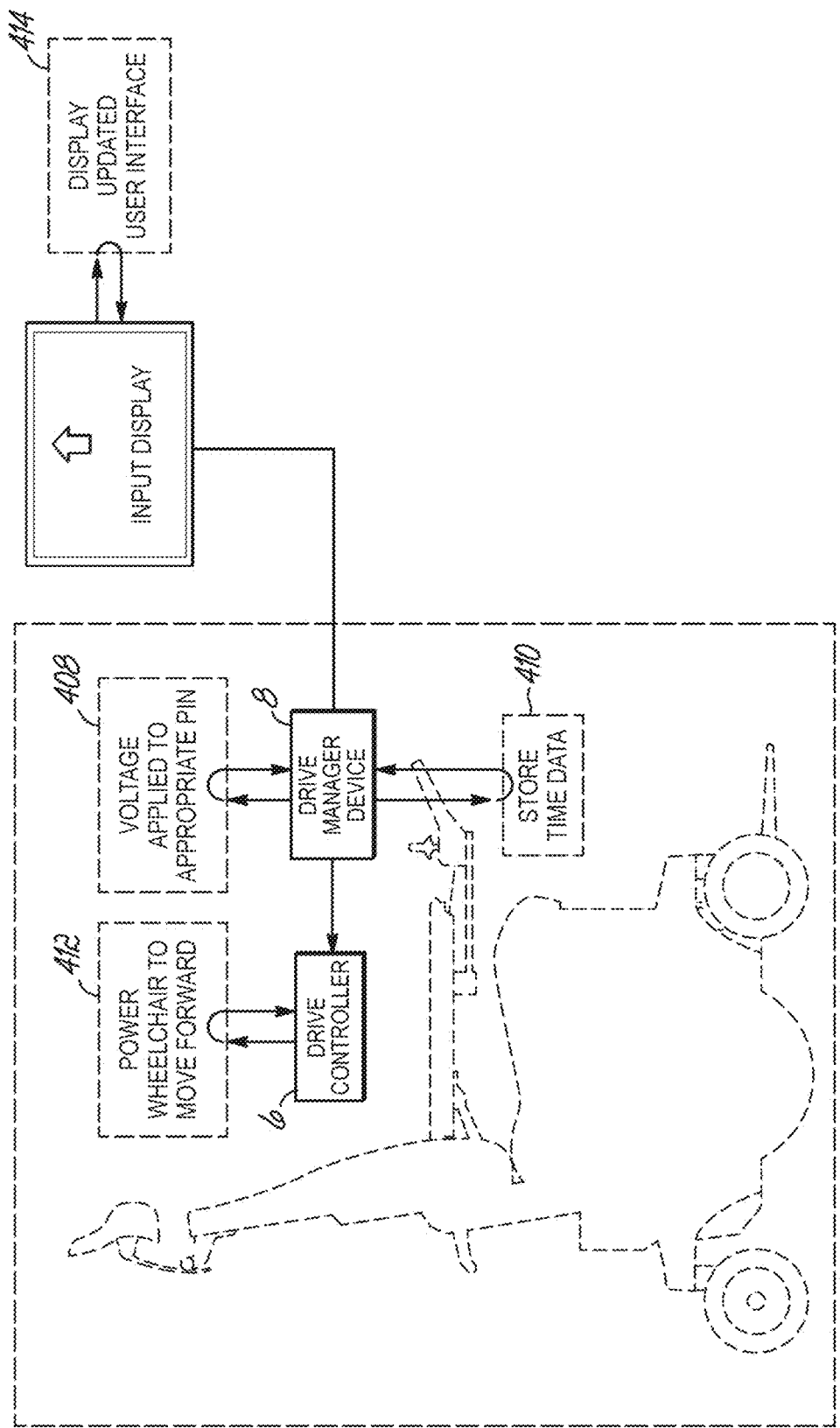
FIG. 4B is a diagram that illustrates, according to the principles of the present invention, a drive manager device causing the power wheelchair to move in the forward direction.

FIG. 4B is a diagram that illustrates, according to the principles of the present invention, the drive manager device 8 causing the power wheelchair 4 to move in the forward direction. For example, the drive manager device 8 processes the received command data to identify the appropriate command. Next, and as shown by reference number 408, the drive manager device 8 causes voltage to be applied to the appropriate pin. For example, the 9-pin interface has pins corresponding to different directional commands, such that one of the pins corresponds to movement in the forward direction. In this case, the drive manager device 8 causes voltage to be applied to the pin that corresponds to the movement in the forward direction. This causes voltage to be sent through the pin of the 9-pin interface to the drive controller 6.

As shown by reference number 410, the drive manager device 8 stores the time data. For example, the time data specifies a maximum duration during which the power wheelchair 4 is permitted to move in the forward direction, and by storing the time data, the drive manager device 8 references the time data to ensure that the power wheelchair 4 is not permitted to move in the forward direction for a duration that exceeds the duration specified by the time data.

As shown by reference number 412, the drive controller 6 causes the power wheelchair 4 to move in the forward direction. For example, the drive controller 6, based on voltage being received through the pin that corresponds to movement in the forward direction, interacts with one or more motors to cause the power wheelchair 4 to begin to move in the forward direction. To provide a specific example, the driver controller 6, based on the voltage received through the pin, generates electrical signals used to activate the one or more motors of the power wheelchair 4.

In some embodiments, such as when the duration specified by the time data has lapsed, the drive manager device 6 causes a voltage offset to be applied to the pin corresponding to the movement in the forward direction. For example, assume the time data includes a value of five, representing that the power wheelchair 4 is to move in the forward direction for five seconds. After five seconds has lapsed, the drive manager device 6 causes a voltage offset to be applied to the pin corresponding to the movement in the forward direction. The voltage offset is received by the drive controller 6 and causes the drive controller 6 to stop the power wheelchair 4 from continuing to move in the forward direction. In some embodiments, the voltage offset is an increase in voltage relative to the voltage that had been initially applied to the pin. In some embodiments, the voltage offset is a different change in voltage (relative to the voltage initially applied to the pin).

As shown by reference number 414, the input collection/display unit 10 displays an updated user interface. For example, the user interface is updated such that the forward directional arrow is highlighted or accentuated to show that the power wheelchair 4 is moving in the forward direction. In some embodiments, the user interface updates to display a timer indicating a duration during which the power wheelchair 4 is to continue to move in the forward direction. This alerts the patient that, at the expiration of the duration of the timer, that the patient will have to gaze or look at a directional arrow in order for the power wheelchair 4 to continue moving. In some embodiments, such as when an automatic drive timer is not used, the patient has to continue to gaze or look at the forward directional arrow in order for the power wheelchair 4 to continue to move in the forward direction.

In this way, the patient uses his or her eyes to cause the power wheelchair 4 to move in the forward direction.

Figure 4C:
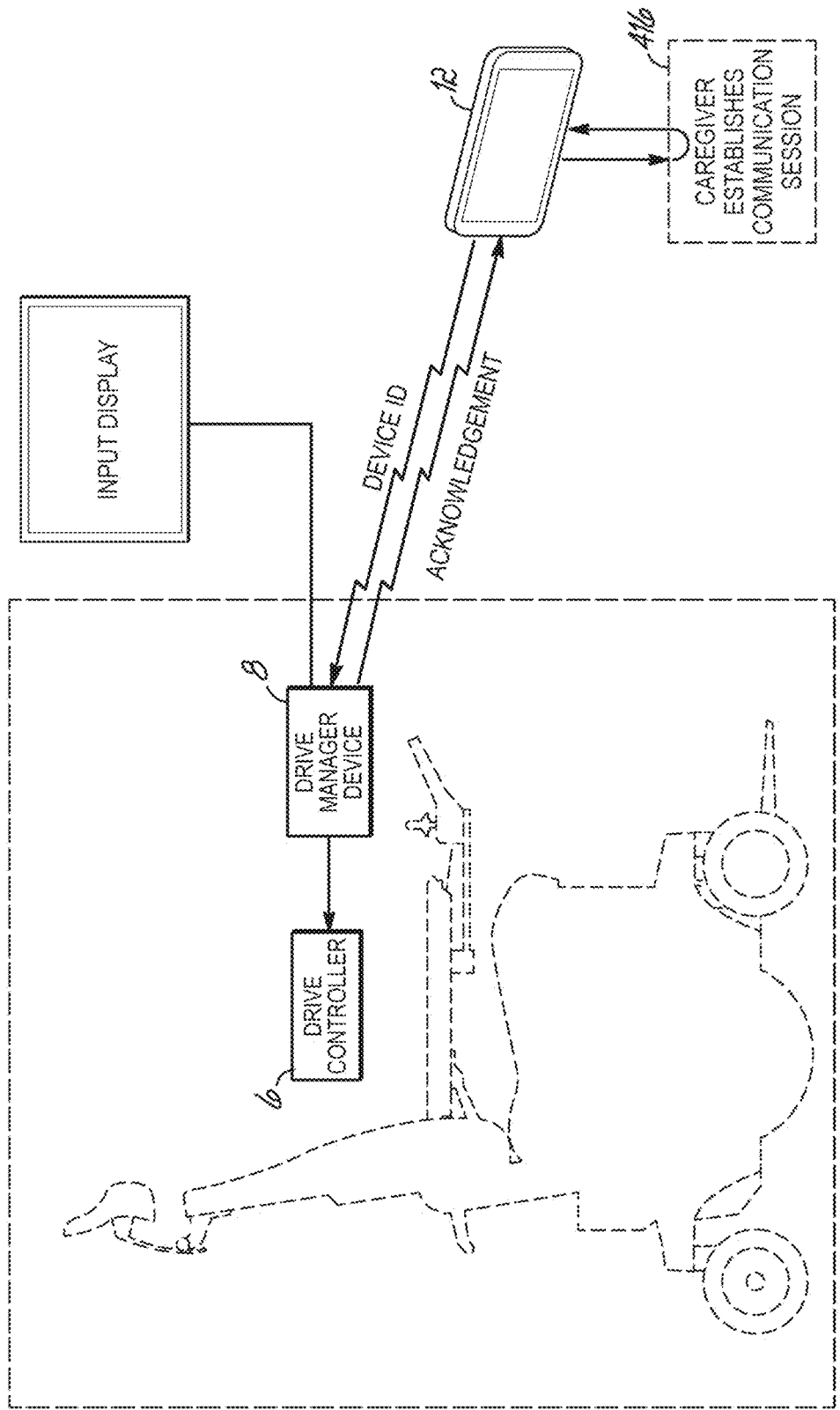
FIG. 4C is a diagram that illustrates, according to the principles of the present invention, a caregiver unit establishing a communication session with the drive manager device.

FIG. 4C is a diagram that illustrates, according to the principles of the present invention, the caregiver unit 12 establishing a communication session with the drive manager device 8. As shown by reference number 416, a caregiver interacts with the caregiver unit 12 to establish a communication session with the drive manager device 8. The communication session is a Bluetooth communication session, a Bluetooth Low Energy (BLE) communication session, and/or another type of communication session. The communication session is made over another communication interface (e.g., separate from the USB interface), such as a Bluetooth interface or BLE interface.

To establish a Bluetooth communication session, the caregiver toggles a Bluetooth connection setting on the caregiver unit 12 and may select the wheelchair control application in a Bluetooth connection prompt. This causes the caregiver unit 12 to provide, to the drive manager device 8, a request to establish a Bluetooth communication session. The request may include a device identifier of the caregiver unit 12. The device identifier, for example, includes a mobile device identifier (MDI), a unique device identifier (UDI), and/or a similar type of identifier that can be used to uniquely identify the caregiver unit 12. Continuing with the example, the drive manager device 8 processes the request and provides the caregiver unit 12 with an acknowledgement indicating that the Bluetooth communication session has been established.

In some embodiments, the drive manager device 8 stores the device identifier. For example, the drive manager device 8 stores the device identifier such that the device identifier may be referenced to ensure that only one device is permitted to control the power wheelchair 4 at a given time.

In some embodiments, the communication session between the caregiver unit 12 and the drive manager device 8 is established using one or more other means. For example, the communication session is established using a universal serial bus (USB) device discovery process, an Ethernet and link level discovery protocol, an internet protocol (IP) multicast domain name server (DNS), Wi-Fi, and/or the like.

In this way, the caregiver uses the caregiver unit 12 to initiate and establish a communication session with the drive manager device 8, even while the patient is actively driving the power wheelchair 4. As such, two separate devices are permitted to communicate with the power wheelchair 4 at the same time. As will be shown below, this allows control of the power wheelchair 4 to be quickly changed between patient and caregiver, while also permitting the caregiver to perform emergency actions even while the patient is controlling the power wheelchair 4.

Figure 4D:
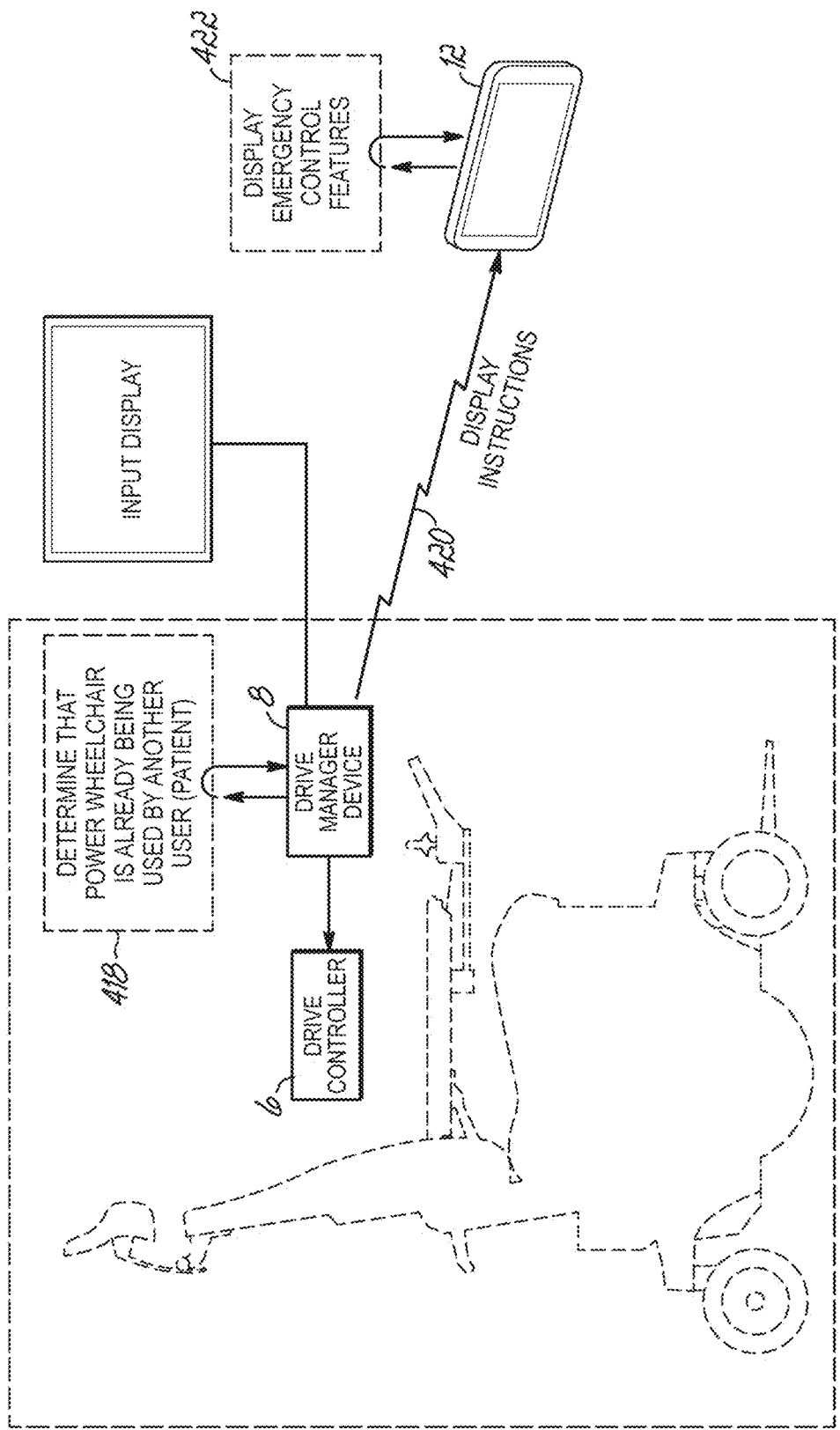
FIG. 4D is a diagram that illustrates, according to the principles of the present invention, the drive manager device assigning or allocating control functionality when multiple devices are connected to the power wheelchair.

FIG. 4D is a diagram that illustrates, according to the principles of the present invention, the drive manager device 8 assigning or allocating control functionality when multiple devices are connected to the power wheelchair 4. For example, the input collection/display unit 10 is connected to the drive manager device 8 using the USB interface, and the caregiver unit 12 is connected to the drive manager device 8 using the Bluetooth interface.

As shown by reference number 418, the drive manager device 8 determines that the power wheelchair 4 is already being controlled by another user (e.g., the patient). For example, while the drive manager device 8 has allowed the caregiver unit 12 to connect and establish a communication session, the drive manager device 8 additionally determines that the power wheelchair 4 is already being controlled by the input collection/display unit 10. In this way, the drive manager device 8 prevents two separate devices from driving the power wheelchair 4 concurrently.

In some embodiments, the drive manager device 8 determines that the power wheelchair is being controlled by another user based on the fact that the caregiver unit 12 has connected to the drive manager device 8 using the Bluetooth interface, while the power wheelchair 4 is presently being controlled by the input collection/display unit 10 using the USB interface.

In some embodiments, the drive manager device 8 determines that the power wheelchair 4 is being controlled by another user based on receiving the device identifier of the caregiver unit 12. For example, the drive manager device 8 stores a device identifier of the device that connects using the Bluetooth interface. In this case, because the caregiver unit 12 established a communication session using the Bluetooth interface, the drive manager device 8 has stored the device identifier and is able to identify which communications are received from the caregiver unit 12 (as opposed to the input collection/display unit 10) based on the device identifier. In this way, the drive manager device prevents two users from concurrently operating or driving the power wheelchair 4.

As shown by reference number 420, the drive manager device 8 provides, to the caregiver unit 12, display instructions indicating that only emergency control features are to be provided for display via a user interface of the wheelchair control application. As shown by reference number 422, the caregiver unit 12 displays the emergency control features on the user interface of the wheelchair control application. For example, the caregiver unit 12 displays an emergency control feature that allows the caregiver to perform an emergency stop or pause of the power wheelchair 4. However, because the power wheelchair 4 is being operated by the patient, the user interface will not display directional arrows that would ordinarily be shown as part of a drive mode of the wheelchair control application.

In this way, two separate devices concurrently communicate with the drive manager device 8. This improves the safety of the patient by providing a fast and efficient way for the caregiver to take over and control the power wheelchair 4 in the event of an emergency. Furthermore, by permitting concurrent communication, while preventing concurrent drive control, the drive manager device 8 preserves the safety of the patient while still retaining the ability of the caregiver to step in should an emergency occur. Still further, by allowing the caregiver to connect to the drive manager device 8 using the caregiver unit 12, which may be a mobile phone, the caregiver is enabled to walk beside the patient instead of behind the patient. This allows the caregiver to engage with the patient in a more natural manner and puts the caregiver in a better position to take care of the needs of the patient while they are traveling.

FIG. 4E is a diagram that illustrates, according to the principles of the present invention, the patient using eye driving technology to request to stop or relinquish control of the power wheelchair 4. For example, the patient interacts with the user interface of the drive mode of the wheelchair control application to request to stop or relinquish control of the power wheelchair 4. The user interface displays a stop button. The patient gazes or looks at the stop button for a threshold time period. As shown by reference number 424, the sensor of the input collection/display unit 10 captures image data of the patient's eyes and/or face while the patient is gazing or looking at the stop button.

As shown by reference number 426, the input collection/display unit 10 processes the image data to determine the command issued by the patient. For example, the input collection/display unit 10 processes the image data using one or more techniques or methods described elsewhere herein and, based on that processing, determines that the command issued by the patient is a command to stop or relinquish control of the power wheelchair 4.

As shown by reference number 428, the input collection/display unit 10 provides stop command data to the drive manager device 8. For example, the input collection/display unit 10 provides the stop command data to the drive manager device 8 via the USB interface.

In this way, the patient uses his or her eyes to request to stop or relinquish control of the power wheelchair 4.

Figure 4F:
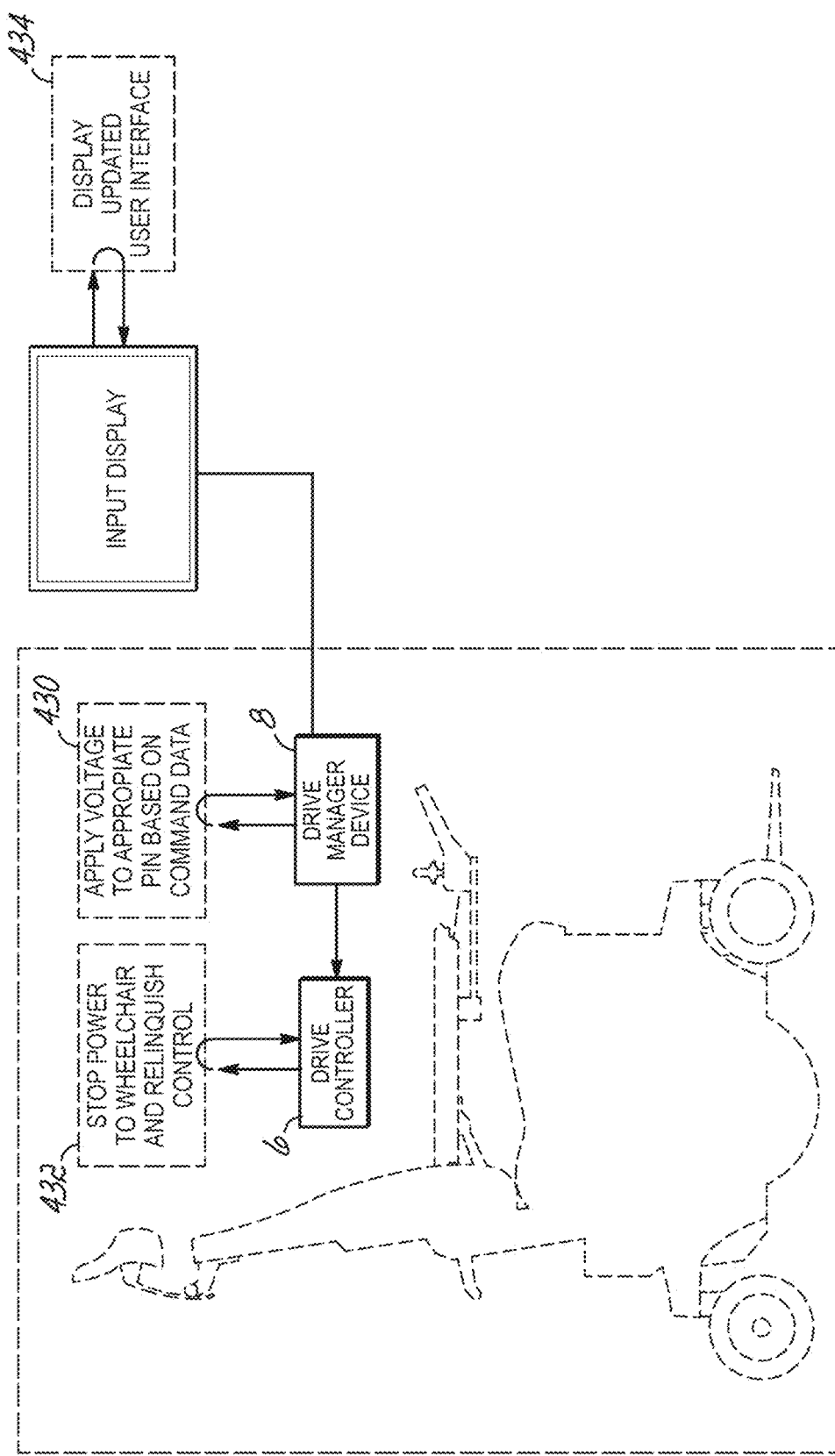
FIG. 4F is a diagram that illustrates, according to the principles of the present invention, the drive manager device exiting the drive mode such that the patient is no longer able to control the power wheelchair using the eye driving technology.

FIG. 4F is a diagram that illustrates, according to the principles of the present invention, the drive manager device 8 exiting the drive mode such that the patient is no longer able to control the power wheelchair 4 using the eye driving technology. For example, the drive manager device 8 processes the received stop command data to identify that the patient has requested to stop the power wheelchair 4. Next, as shown by reference number 430, the drive manager device 8 causes a voltage to be applied to a particular pin of the 9-pin interface. For example, the drive manager device 8 causes a voltage offset to be applied to the pin corresponding to the command to move in the forward direction, causing the offset voltage to be sent through the pin and to the drive controller 6, thereby allowing the power wheelchair 4 to be stopped.

As shown by reference number 432, the drive controller 6 stops or relinquishes the patient's control of the power wheelchair 4. For example, the drive controller 6, based on the offset voltage being provided through the pin corresponding to the command to move in the forward direction, causes a breaking mechanism to stop the power wheelchair 4 from continuing to move in the forward direction.

As shown by reference number 434, the input collection/display unit 10 displays an updated user interface. For example, the user interface is updated such that the forward directional arrow is no longer highlighted or accentuated. Instead, a stop button may be highlighted or accentuated.

In some embodiments, a first device is controlling the power wheelchair 4 and a second device will pause or stop the power wheelchair 4. For example, the input collection/display unit 10 is controlling the power wheelchair 4. In this case, a user interface of the wheelchair control application is provided for display on the caregiver unit 12 and includes emergency stop commands (e.g., stop and pause). As such, the caregiver can use the caregiver unit 12 to perform an emergency stop of the power wheelchair 4, such as by selecting a stop button or a pause button displayed on the user interface of the wheelchair control application. Similarly, the caregiver could be controlling the power wheelchair 4 and the patient could select the stop or pause button (e.g., using the eye gaze technology) to cause the drive manager device 8 to perform an emergency stop of the power wheelchair 4.

In this way, the drive manager device 8 stops the power wheelchair 4, thereby freeing up control of the power wheelchair 4 so that another user can step in and drive the power wheelchair 4. Furthermore, by allowing a separate device to perform an emergency stop of the power wheelchair 4, the safety of the patient is improved by allowing two separate users to stop the vehicle. This could be useful for any number of different situations, such as if an object is on course to collide with the power wheelchair 4 but the object is not within the patient's line of sight, if the patient has a medical emergency that causes them to be temporarily unable to control the power wheelchair 4, and/or the like.

Figure 4G:
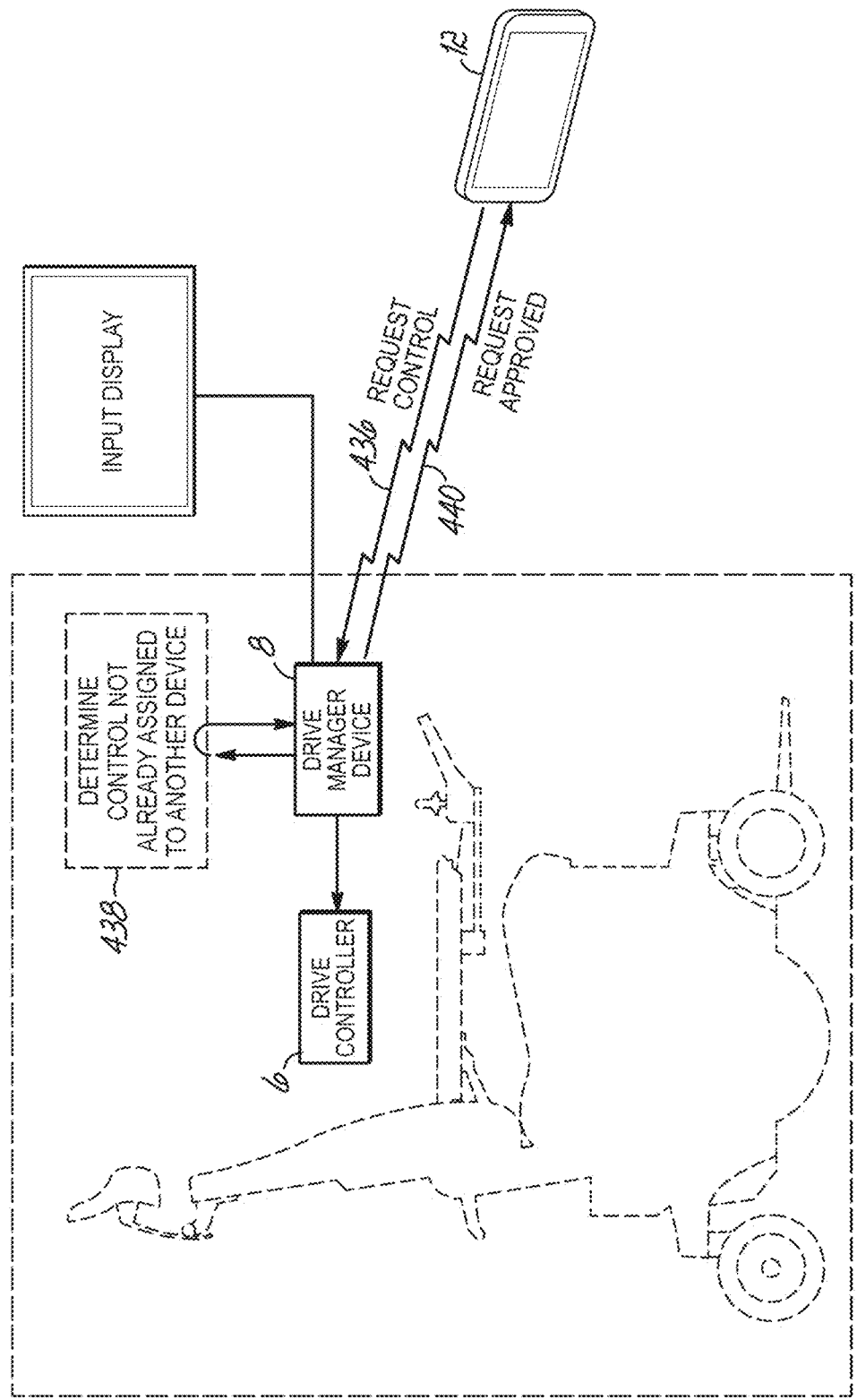
FIG. 4G is a diagram that illustrates, according to the principles of the present invention, the drive manager device granting control of the power wheelchair to the caregiver unit.

FIG. 4G is a diagram that illustrates, according to the principles of the present invention, the drive manager device 8 granting control of the power wheelchair to the caregiver unit 12. As shown by reference number 436, the caregiver unit 12 may provides a request to control the power wheelchair 4 to the drive manager device 8. For example, the caregiver interacts with a user interface of the wheelchair control application, such as by selecting a start button, to request to control the power wheelchair 4. To request control, the caregiver unit 12 generates start command data and provides the start command data and/or the device identifier of the caregiver unit 12 to the drive manager device 8. The start command data and/or the device identifier is provided over the Bluetooth interface.

As shown by reference number 438, the drive manager device 8 determines that control of the power wheelchair 4 has not already been assigned to another device. For example, the drive manager device 8 determines that the control of the power wheelchair 4 has not already been assigned to another device using one or more techniques described elsewhere herein.

As shown by reference number 440, the drive manager device 8 provides, to the caregiver unit 12, a message indicating that the request to control the power wheelchair 4 has been granted. This message is provided over the Bluetooth interface. In some embodiments, the drive manager device 8, based on approving the request to control the power wheelchair 4, causes the user interface of the caregiver unit 12 to update to display a set of drive controls. The set of drive controls include a virtual joystick and/or one or more directional arrow buttons that can be used in conjunction with the virtual joystick to provide additional drive support.

In this way, the caregiver unit 12 is able obtain control of the power wheelchair 4 shortly after the patient's control has been removed.

Figure 4H:
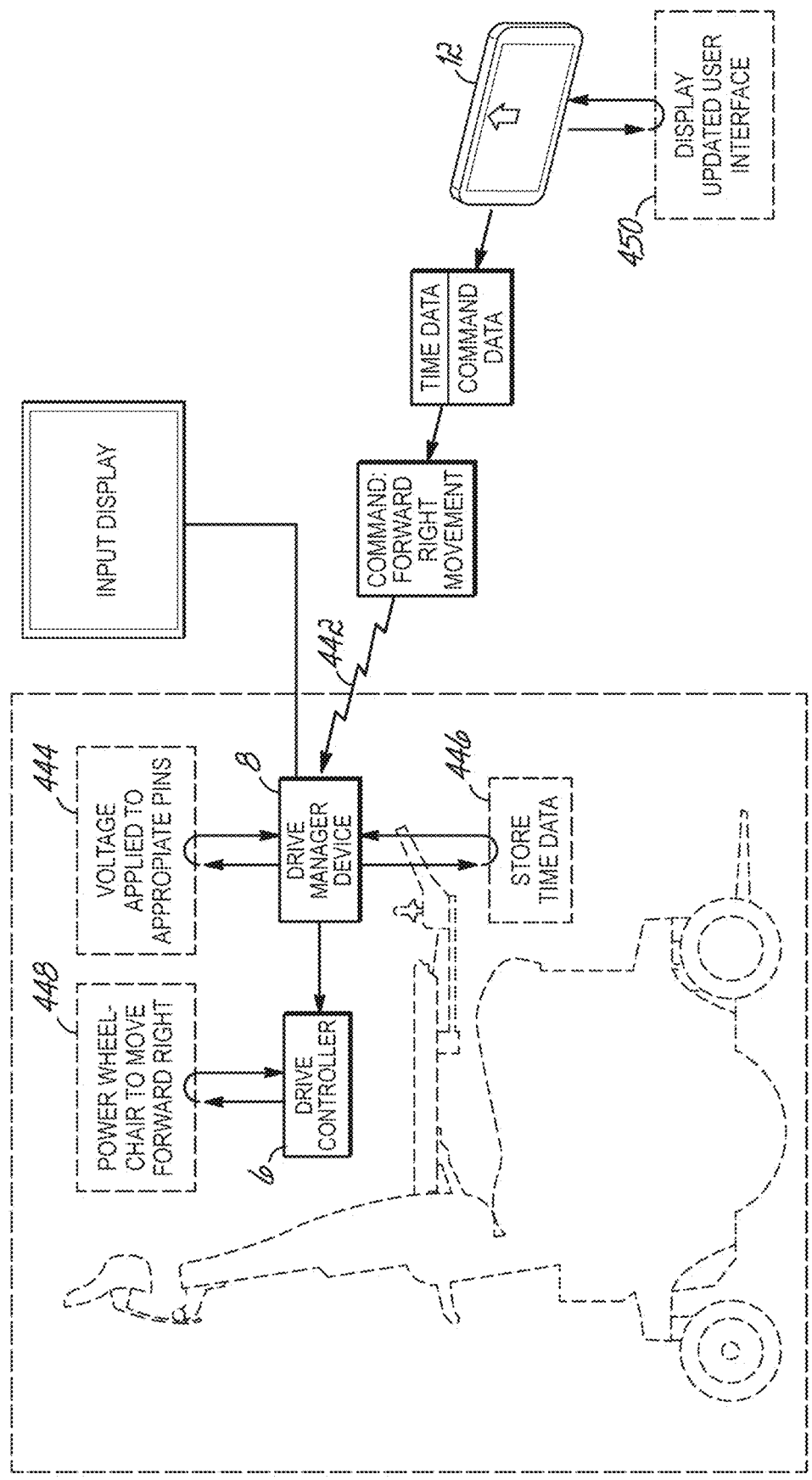
FIG. 4H is a diagram that illustrates, according to the principles of the present invention, the caregiver unit controlling the power wheelchair.

FIG. 4H is a diagram that illustrates, according to the principles of the present invention, the caregiver unit 12 controlling the power wheelchair 4. As shown by reference number 442, the caregiver unit 12 provides, to the drive manager device 8, command data and/or time data corresponding to a command made by the caregiver. For example, the user interface of the wheelchair control application displayed on the caregiver unit 12 shows a virtual joystick that may be used to operate the power wheelchair 4. To operate the power wheelchair 4, the caregiver moves or presses the virtual joystick in a particular direction. In the example shown, the caregiver moves or presses the virtual joystick in a forward-right direction to generate a command to move the power wheelchair 4 in a forward-right direction. This causes forward-right command data and/or time data corresponding to the command to be provided to the drive manager device 8.

As shown by reference number 444, the drive manager device 8 causes voltage to be applied to the appropriate pins. For example, the drive manager device 8 processes the received forward-right command data to identify that the caregiver is requesting to move in the forward-right direction. Next, the drive manager device 8 causes voltage to be applied to a first pin corresponding to the command to move the power wheelchair 4 in a forward direction and to a second pin corresponding to a command to move the power wheelchair 4 in a right direction. This causes the voltage to be sent through the pins and to the drive controller 6.

As shown by reference number 446, the drive manager device 8 stores time data. For example, the drive manager device 8 stores time data that may be later referenced to ensure that the power wheelchair 4 is not permitted to move in the forward-right direction for a duration that exceeds the duration specified by the time data.

As shown by reference number 448, the drive controller 6 causes the power wheelchair 4 to move in the forward-right direction. For example, based on voltage being provided through the pins corresponding to the movement in the forward-right direction, the drive controller 6 interacts with one or more motors and/or a mechanical actuator to cause the power wheelchair 4 to begin to move in the forward-right direction.

As shown by reference number 450, the caregiver unit 12 displays an updated user interface. For example, the user interface is updated such that the forward-right directional arrow is highlighted or accentuated to show that the power wheelchair 4 is moving in the forward-right direction.

The caregiver can interact with a user interface of the caregiver unit 12 to power off the power wheelchair 4. For example, the caregiver touches or presses on a power button displayed on the user interface, causing the caregiver unit 12 to generate power command data. The caregiver unit 12 provides the power command data to the drive manager device 8. The drive manager device 8, based on the power command data, causes the drive controller 6 to turn off the power wheelchair 4. For example, the drive manager device 8 causes an offset voltage to be applied to the drive controller 6 via the power toggle interface (e.g., a 3.5 mm interface). In this way, the caregiver uses the caregiver unit 12 to toggle off the power of the power wheelchair 4.

By allowing the control of the power wheelchair 4 to be seamlessly changed between patient and caregiver, the drive manager device 8 improves overall safety of the power wheelchair 4 by allowing the patient an easy way to transfer control the power wheelchair 4. Furthermore, by allowing the caregiver unit 12 to communicate with the power wheelchair 4 using a wireless interface (e.g., a Bluetooth interface), the caregiver is provided with the freedom of movement to walk anywhere in a vicinity of the power wheelchair 4, thereby allowing the caregiver to better monitor the patient, to engage in a conversation with the patient while walking next to him or her, and/or the like.

While one or more embodiments described herein refer to control shifting with respect to driving the power wheelchair 4, it is to be understood that this is provided by way of example. In practice, control shifting may be applied in the same manner to other forms of control, such as by shifting the control of the power wheelchair 4 between patient and caregiver when adjusting a position of the seat of the power wheelchair 4. Furthermore, while one or more embodiments describe the patient as powering on the power wheelchair 4 and the caregiver as powering off the power wheelchair 4, it is to be understood that this is provided by way of example. In practice, either device may be used to toggle the power of the power wheelchair 4.

FIGS. 5A-5E, FIG. 6, FIGS. 7A and 7B, and FIGS. 8A and 8B are diagrams that illustrate one or more example user interfaces of the wheelchair control application. In creating its working prototypes of the present invention, new, inventive, and ornamental display screens have been generated that facilitate a user's interaction with the system. Additional new ornamental display screens, also referred to as user interfaces, or graphical user interfaces, may be created as the system evolves toward eventual commercialization. For example, darker input icons could be implemented to provide more contrast to the viewer/driver. Some of the figures show current examples of such display screens. Applicant reserves the right to pursue design patent protection for one or more of these user interfaces in the United States.

Figure 5A:
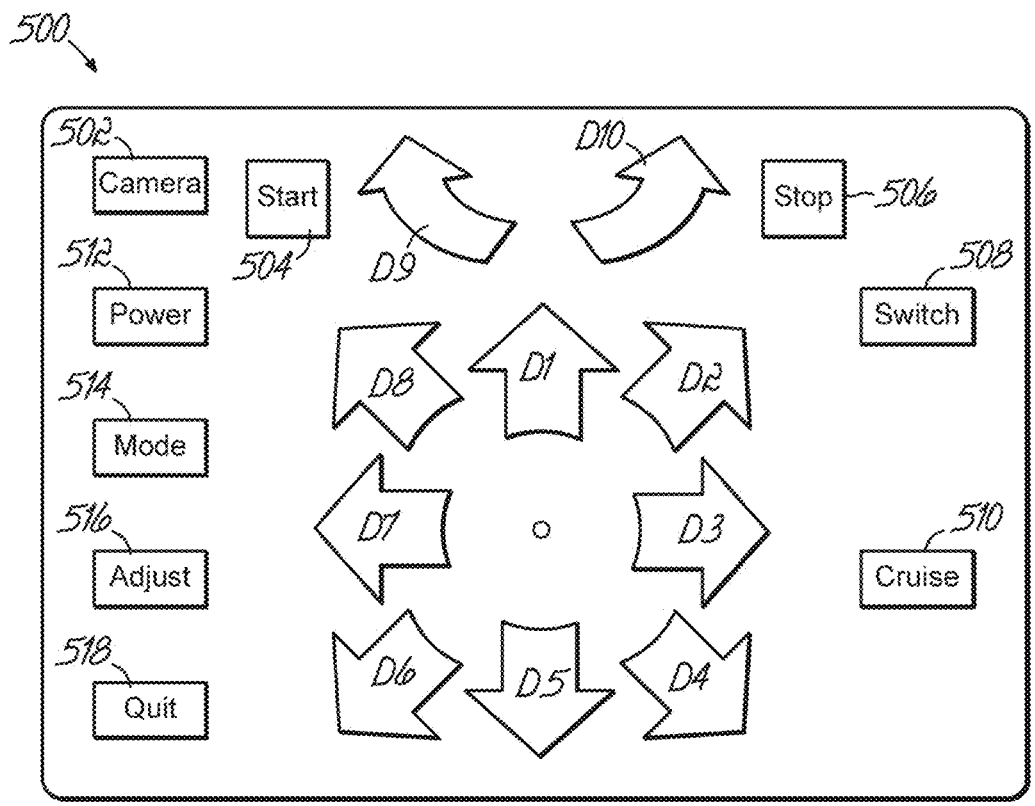
FIG. 5A is a diagram that illustrates, according to the principles of the present invention, an example user interface of a wheelchair control application that is displayed by an input collection/display unit.

FIG. 5A is a diagram that illustrates, according to the principles of the present invention, an example user interface 500 of the wheelchair control application that is displayed by the input collection/display unit 10. The example user interface 500 includes a camera 502 and a set of display buttons, such as a start button 504, a stop button 506, a switch button 508, a cruise control button 510, a power button 512, a drive mode button 514, a seat adjustment button 516, and a quit button 518. The set of display buttons further include buttons depicting a set of directional arrows, which are shown as D1 through D10.

The camera 502 is an image capturing device that is used to capture image data of the patient sitting in the power wheelchair 4. The start button 504 is used to start the drive mode. For example, the patient selects the drive mode by directing his or her gaze toward the start button for a threshold time period. This causes the camera 502 to begin capturing image data of the patient and causes the example user interface 500 to update to display the buttons depicting the set of directional arrows. In the example shown, the set of directional arrows include eight directional arrows in the middle of the user interface, such as a forward directional arrow (D1), a forward-right directional arrow (D2), a right directional arrow (D3), a backward-right directional arrow (D4), a backward directional arrow (D5), a backward-left directional arrow (D6), a left directional arrow (D7), and a forward-left directional arrow (D8). The two directional arrows at the top of the example user interface 500 include a nudge left directional arrow (D9) and a nudge right directional arrow (D10). These directional arrows are used to move the power wheelchair 4 slightly left or slightly right (e.g., relative to the forward direction).

The stop button 506 allows the patient to stop the power wheelchair 4 at any time. By interacting with the stop button 506, the patient will stop the drive mode feature of the wheelchair control application. This causes the buttons depicting the set of directional arrows to disappear from the example user interface 500.

The switch button 508 is a button that is used to signal a third-party assistive device. For example, the drive manager device 8 includes a switch and multiple communication interfaces (e.g., including a power toggle or 3.5 mm interface). The switch and multiple communication interfaces permits the switch button 508 to be used to signal a third-party assistive device. The third-party assistive device is an add-on safety system that includes hardware and/or software components.

The cruise control button 510 is a button that, when selected by the patient, allows the power wheelchair 4 to continue to move automatically in a current direction. For example, if the cruise control button 510 is selected, and the power wheelchair 4 is moving in the forward direction, the power wheelchair 4 continues to move in the forward direction until a stop condition occurs. A stop condition occurs when the patient de-selects the cruise control button 510, when a direction of the power wheelchair 4 changes, when a timer expires that specifies a maximum duration in which the cruise control button 510 can remain selected, and/or the like.

The power button 512 is a button that allows the patient to power on the power wheelchair 4. For example, the patient looks or gazes at the power button 512 for a threshold time period. The camera 502 generates image data capturing the patient's gaze, and the input collection/display unit 10 processes the image data to identify the command made by the patient (e.g., a request to power on the power wheelchair 4). The input collection/display unit 10 provides command data corresponding to the identified command to the drive manager device 8. The drive manager device 8, based on the received command data, powers on the drive controller 6 by causing voltage to be applied to the appropriate pin.

The mode button 514 is a button that allows the patient to change the mode of operation. In some embodiments, the mode button is used to cycle through the different modes of control provided by the power wheelchair 4 (e.g., a drive mode, a seat adjustment mode, etc.). For example, each time the mode button 514 is selected, a next available mode in the cycle is selected. To provide a specific example, the patient selects the mode button 514 to select the drive mode. This causes the example user interface 500 to update to display the start button 504 for the drive mode. If the user selects the start button 504, the example user interface 500 updates to display directional arrow buttons corresponding to different directional movements. In some embodiments, a driver controller display is available and includes a menu that allows a user to navigate and select a desired mode.

The seat adjustment button 516 is used to adjust a position of the seat of the power wheelchair 4 and/or any other related settings. For example, when the patient selects the seat adjustment button 516, the user is permitted to enter the seat adjustment mode. This will cause the example user interface 500 to update such that buttons depicting directional arrows (e.g., which correspond to different seat movements) are provided for display. In some embodiments, the seat adjustment button 516 is used to navigate a drive controller 6 menu. The quit button 518 is a button that allows the patient to quit out of a current user interface of the wheelchair control application.

The set of buttons depicted in example user interface 500 are provided by way of example. In practice, example user interface 500 may display a subset of these buttons at any given time. For example, the start button 504 and stop button 506 may only appear on the example user interface 500 if the patient has selected the drive mode button 514 or the seat adjustment mode button 516. To provide another example, the buttons depicting the set of directional arrows may only appear on the example user interface 500 if the patient has selected the start button 504.

Furthermore, additional buttons may be added to the example user interface 500 and buttons may be presented in orders different than what is shown by example user interface 500. For example, after the patient has selected the start button 504, a pause button may be displayed on the example user interface 500. To provide another example, instead of showing a mode button 514, the example user interface 500 might have a separate button for respective modes, such as by having a drive mode button and a seat adjustment mode button.

Figure 5B:
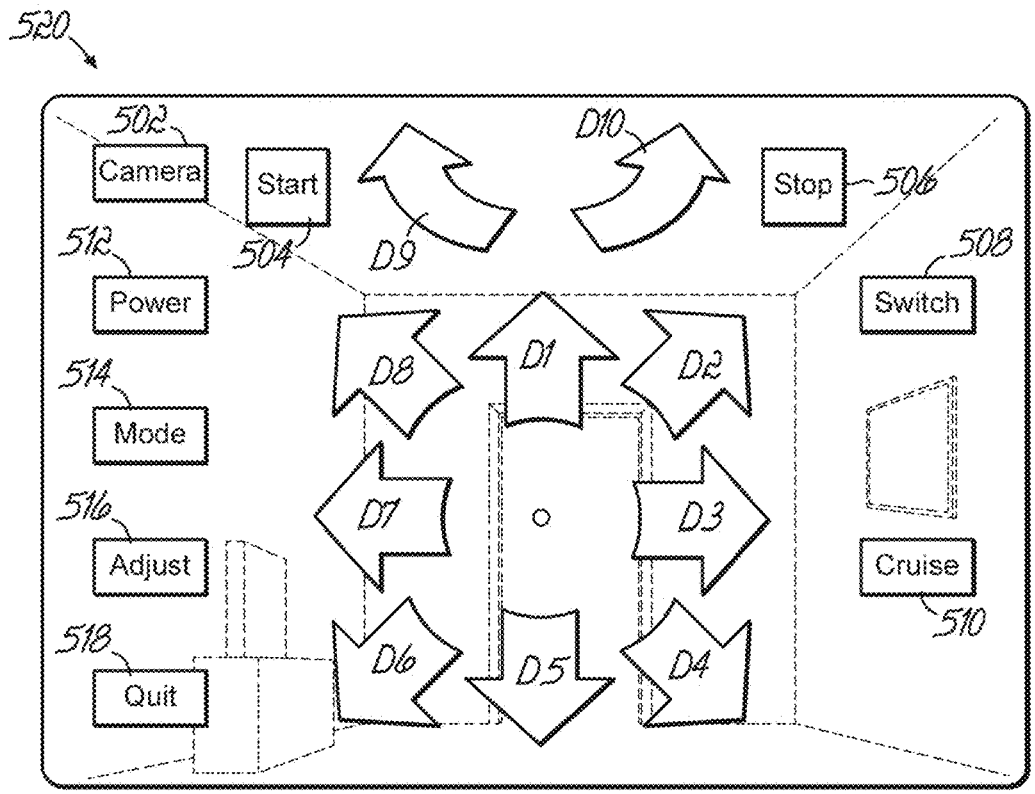
FIG. 5B is a diagram that illustrates, according to the principles of the present invention, an example user interface of the wheelchair control application that is displayed by the input collection/display unit.
Figure 5C:
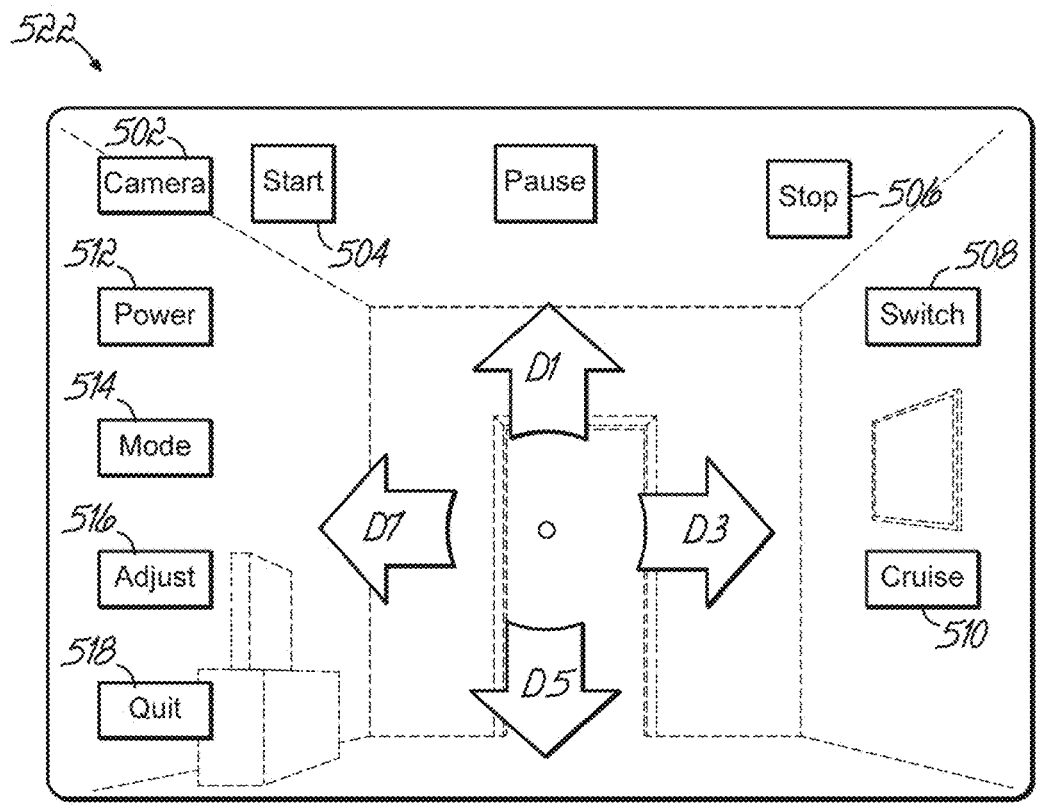
FIG. 5C is a diagram that illustrates, according to the principles of the present invention, an example user interface of the wheelchair control application that is displayed by the input collection/display unit.
Figure 5D:
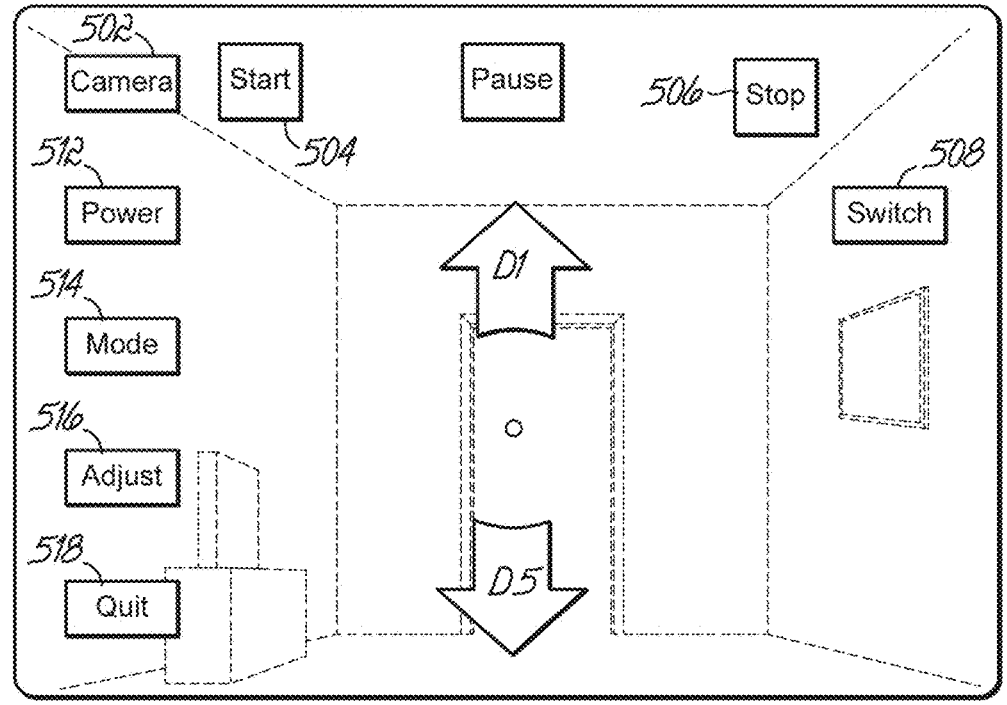
FIG. 5D is a diagram that illustrates, according to the principles of the present invention, an example user interface of the wheelchair control application that is displayed by the input collection/display unit.
Figure 5E:
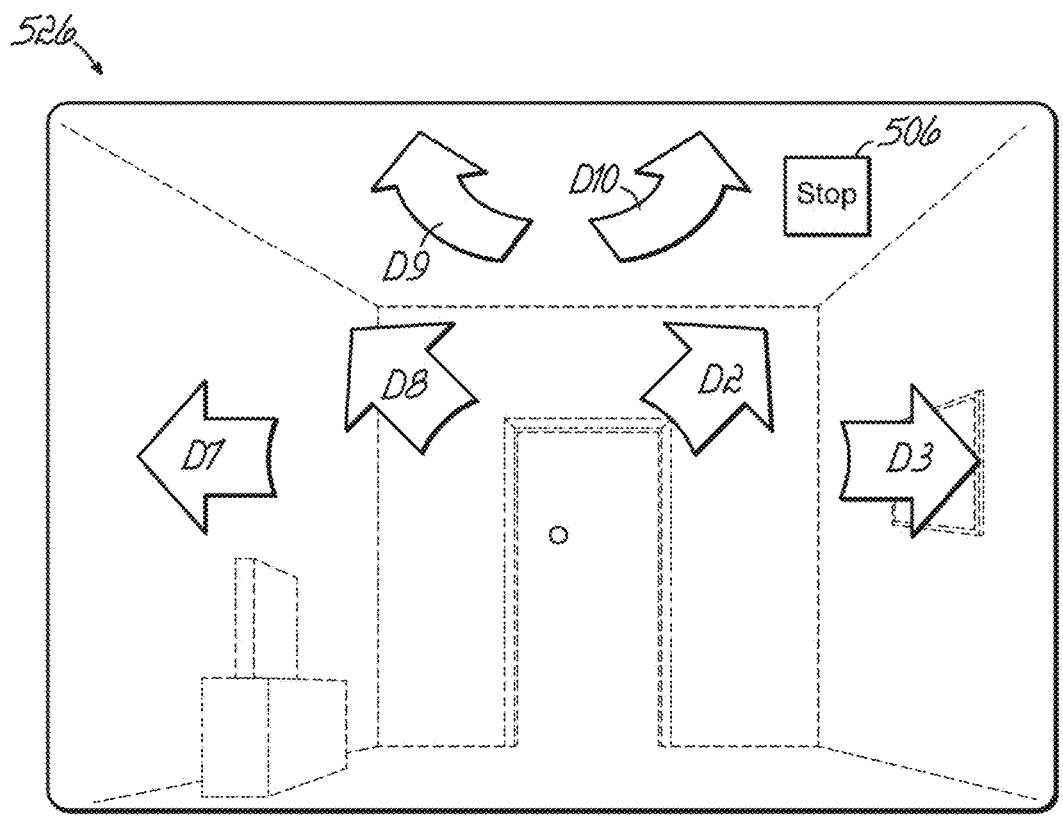
FIG. 5E is a diagram that illustrates, according to the principles of the present invention, an example user interface of the wheelchair control application that is displayed by the input collection/display unit.

FIG. 5B is a diagram that illustrates, according to the principles of the present invention, an example user interface 520 of the wheelchair control application that is displayed by the input collection/display unit 10. FIG. 5C is a diagram that illustrates, according to the principles of the present invention, an example user interface 522 of the wheelchair control application that is displayed by the input collection/display unit 10. FIG. 5D is a diagram that illustrates, according to the principles of the present invention, an example user interface 524 of the wheelchair control application that is displayed by the input collection/display unit 10. FIG. 5E is a diagram that illustrates, according to the principles of the present invention, an example user interface 526 of the wheelchair control application that is displayed by the input collection/display unit 10.

Figure 6:
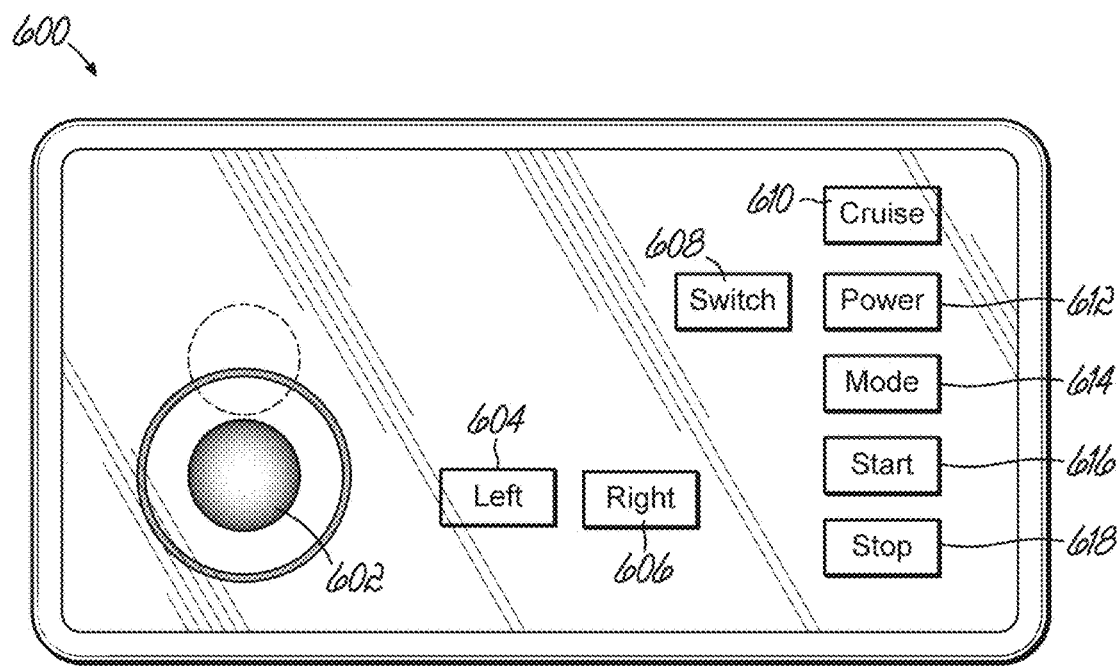
FIG. 6 is a diagram that illustrates, according to the principles of the present invention, an example user interface of the wheelchair control application that is displayed by a caregiver unit.

FIG. 6 is a diagram that illustrates, according to the principles of the present invention, an example user interface 600 of the wheelchair control application that is displayed by the caregiver unit 12. The example user interface 600 includes a virtual joystick 602, a nudge left button 604, a nudge right button 606, a switch button 608, a cruise control button 610, a power button 612, a mode button 614, a start button 616, a stop button 618.

The virtual joystick 602 is a virtual object that the caregiver can use to drive the power wheelchair 4 remotely. For example, the caregiver interacts with the virtual joystick 602 to cause the power wheelchair 4 to move in a forward direction, a forward-right direction, a right direction, a backward-right direction, a backward direction, a backward-left direction, a left direction, and a forward-left direction. The nudge left button 604 and the nudge right button 606 compliment the virtual joystick 602 and provide the caregiver with a means to move the power wheelchair 4 slightly to the left or right (relative to a forward direction).

The switch button 608, cruise control button 610, power button 612, mode button 6114, start button 616, and stop button 618 performs functions consistent with that described in connection with FIG. 5.

Figure 7A:
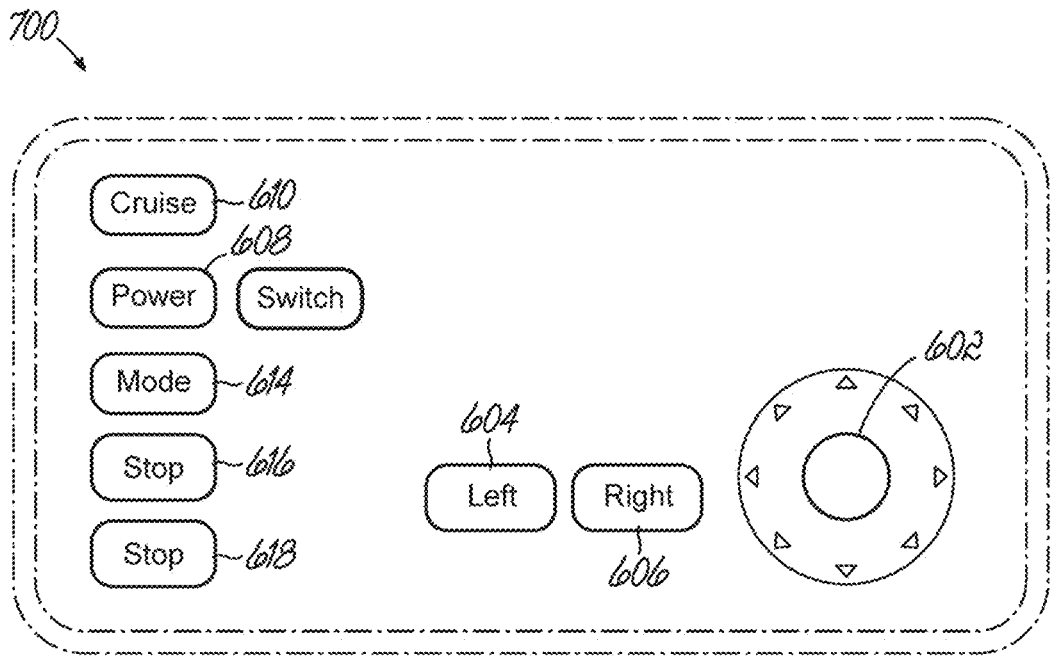
FIG. 7A is a diagram that illustrates, according to the principles of the present invention, an example user interface of the wheelchair control application that is displayed by a caregiver unit.
Figure 7B:
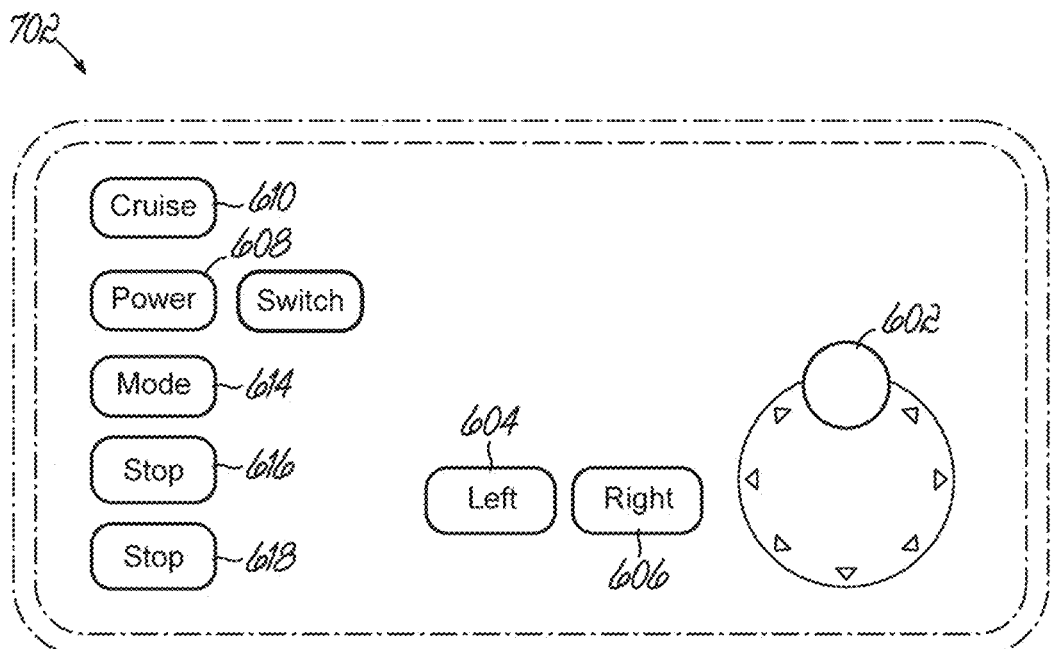
FIG. 7B is a diagram that illustrates, according to the principles of the present invention, an example user interface of the wheelchair control application that is displayed by a caregiver unit.
Figure 8A:
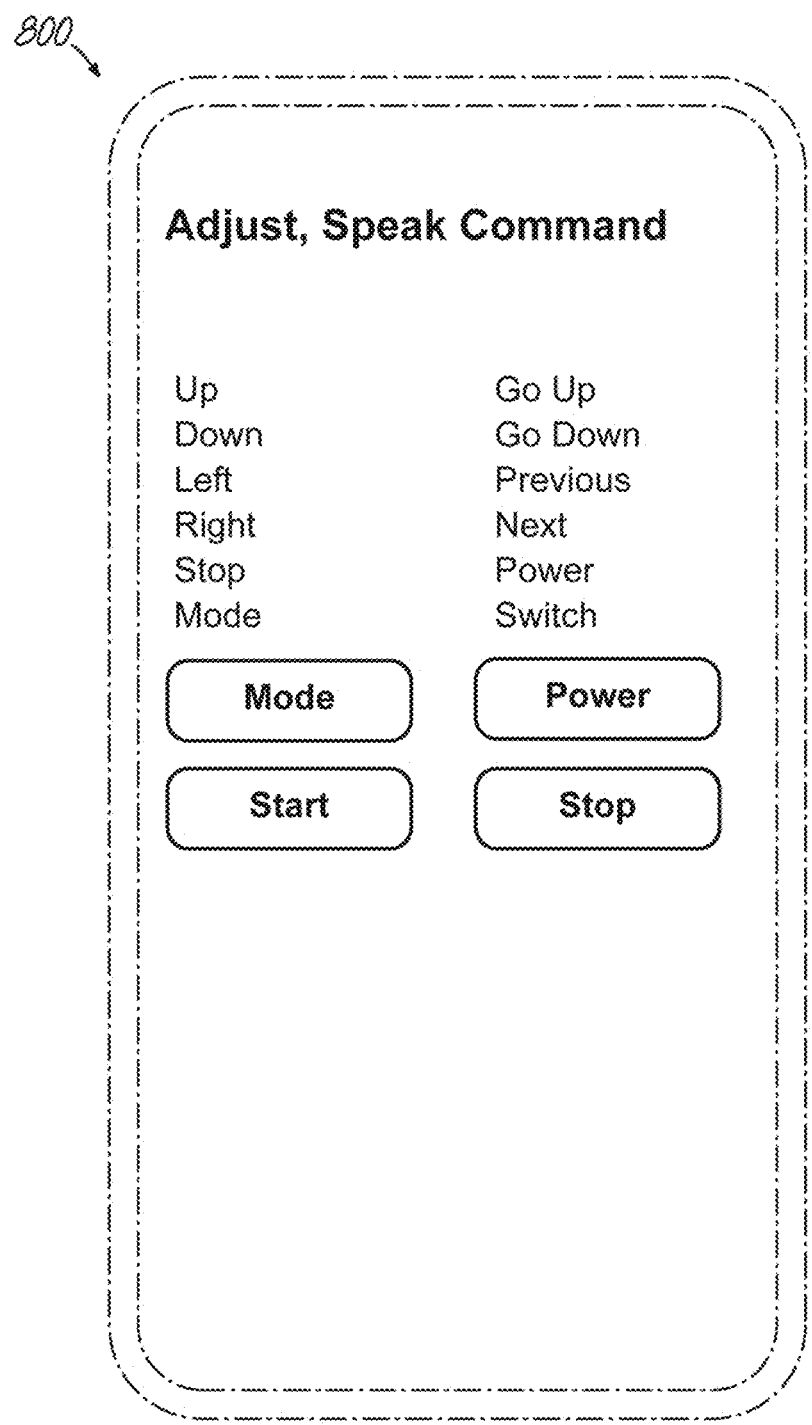
FIG. 8A is a diagram that illustrates, according to the principles of the present invention, an example user interface of the wheelchair control application that is displayed by a caregiver unit.
Figure 8B:
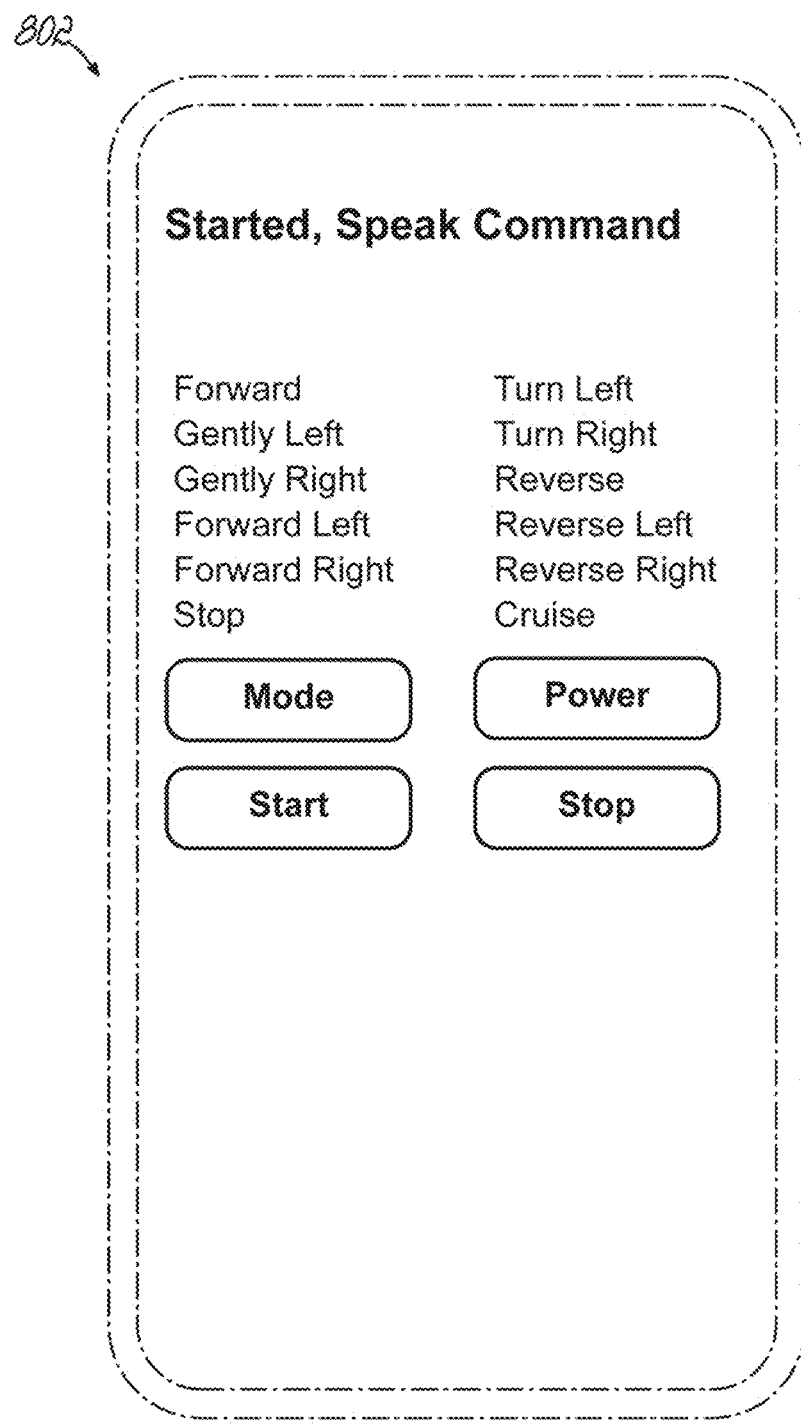
FIG. 8B is a diagram that illustrates, according to the principles of the present invention, an example user interface of the wheelchair control application that is displayed by a caregiver unit.

FIG. 7A is a diagram that illustrates, according to the principles of the present invention, an example user interface 700 of the wheelchair control application that is displayed by a caregiver unit. FIG. 7B is a diagram that illustrates, according to the principles of the present invention, an example user interface 702 of the wheelchair control application that is displayed by a caregiver unit. FIG. 8A is a diagram that illustrates, according to the principles of the present invention, an example user interface 800 of the wheelchair control application that is displayed by a caregiver unit. FIG. 8B is a diagram that illustrates, according to the principles of the present invention, an example user interface 802 of the wheelchair control application that is displayed by a caregiver unit.

The foregoing disclosure provides illustration and description but is not intended to be exhaustive or to limit the embodiments to the precise form disclosed. Modifications and variations may be made in light of the above disclosure or may be acquired from practice of the embodiments.

As used herein, the term "component" is intended to be broadly construed as hardware, firmware, or a combination of hardware and software.

Some embodiments are described herein in connection with thresholds. As used herein, satisfying a threshold may, depending on the context, refer to a value being greater than the threshold, more than the threshold, higher than the threshold, greater than or equal to the threshold, less than the threshold, fewer than the threshold, lower than the threshold, less than or equal to the threshold, equal to the threshold, etc., depending on the context.

Certain user interfaces have been described herein and/or shown in the figures. A user interface may include a graphical user interface, a non-graphical user interface, a text-based user interface, and/or the like. A user interface may provide information for display. In some embodiments, a user may interact with the information, such as by providing input via an input component of a device that provides the user interface for display. In some embodiments, a user interface may be configurable by a device and/or a user (e.g., a user may change the size of the user interface, information provided via the user interface, a position of information provided via the user interface, etc.). Additionally, or alternatively, a user interface may be pre-configured to a standard configuration, a specific configuration based on a type of device on which the user interface is displayed, and/or a set of configurations based on capabilities and/or specifications associated with a device on which the user interface is displayed. Further, the designs shown in one or more of FIG. 5A, FIG. 5B, FIG. 5C, FIG. 5D, FIG. 5E, FIG. 6, FIG. 7A, FIG. 7B, FIG. 8A, and FIG. 8B represent subject matter that applicant considers to be new, original, and ornamental, and that includes subject matter eligible for one or more U.S. continuing design patent applications.

It will be apparent that systems and/or methods described herein may be implemented in different forms of hardware, firmware, and/or a combination of hardware and software. The actual specialized control hardware or software code used to implement these systems and/or methods is not limiting of the embodiments. Thus, the operation and behavior of the systems and/or methods are described herein without reference to specific software code—it being understood that software and hardware can be used to implement the systems and/or methods based on the description herein.

Even though particular combinations of features are recited in the claims and/or disclosed in the specification, these combinations are not intended to limit the disclosure of various embodiments. In fact, some of the features may be combined in ways not currently recited in the claims or expressly disclosed in the specification. Although in the U.S. form of this application each dependent claim may directly depend on only one claim, the disclosure of the various embodiments includes each dependent claim in combination with every other claim in the claim set, as reflected in the published PCT form.

No element, act, or instruction used herein should be construed as critical or essential unless explicitly described as such. Also, as used herein, the articles "a" and "an" are intended to include one or more items, and may be used interchangeably with "one or more." Further, as used herein, the article "the" is intended to include one or more items referenced in connection with the article "the" and may be used interchangeably with "the one or more." Furthermore, as used herein, the term "set" is intended to include one or more items (e.g., related items, unrelated items, a combination of related and unrelated items, and/or the like), and may be used interchangeably with "one or more." Where only one item is intended, the phrase "only one" or similar language is used. Also, as used herein, the terms "has," "have," "having," or the like are intended to be open-ended terms. Further, the phrase "based on" is intended to mean "based, at least in part, on" unless explicitly stated otherwise. Also, as used herein, the term "or" is intended to be inclusive when used in a series and may be used interchangeably with "and/or," unless explicitly stated otherwise (e.g., if used in combination with "either" or "only one of").

We claim:
1. A power wheelchair, comprising:
a plurality of wheels operatively connected to the power wheelchair;
one or more motors operatively associated with the power wheelchair;
a drive controller operatively connected to the one or more motors and mounted to the power wheelchair; and
a drive manager device operatively connected to the drive controller, wherein the drive manager device is to:
communicate with an input collection/display unit via a first communication interface, the input collection/display unit operable by a user in the power wheelchair,
determine a command made by the user by processing command data received in a communication with the input collection/display unit, the command being a request to drive the power wheelchair,
in response to determining the command, cause voltage to be applied through a second communication interface and to the drive controller, wherein the voltage causes the drive controller to interact with the one or more motors to actuate one or more wheels of the plurality of wheels,
communicate, via a third communication interface, with a caregiver unit that is external to the power wheelchair and operable by a caregiver, wherein the first communication interface and the third communication interface permit the input collection/display unit and the caregiver unit to communicate with the drive manager device concurrently,
determine that the input collection/display unit is a controlling device that is presently controlling the power wheelchair, where the caregiver unit is a non-controlling device, and
cause a user interface to be provided for display on the non-controlling device such that the user interface:
omits buttons corresponding to directional drive controls so as to prevent the non-controlling device from driving the power wheelchair, and
displays one or more buttons corresponding to controls other than the directional drive controls.

2. The power wheelchair of claim 1, wherein the first communication interface is a wired interface and the third communication interface is a wireless interface.

3. The power wheelchair of claim 1, wherein the drive manager device is further to:
receive, from the non-controlling device, emergency stop command data associated with a command to stop the power wheelchair; and
cause voltage to be applied through the second communication interface and to the drive controller, wherein the voltage causes the drive controller to interact with a breaking component to stop the power wheelchair.

4. The power wheelchair of claim 1, wherein the drive manager device is further to:
receive, from the input collection/display unit, initial command data indicating a first command made by the user to power on the power wheelchair;
determine, by processing the initial command data, that the first command is to power on the power wheelchair; and
in response to determining that the first command is to power on the power wheelchair, cause voltage to be applied through a fourth communication interface such that power is provided to the drive controller to thereby enable the user to operate the power wheelchair.

5. The power wheelchair of claim 1, wherein the drive manager device is further to:
remove control of the power wheelchair from the input collection/display unit; and
assign control of the power wheelchair to the caregiver unit.

6. The power wheelchair of claim 1, wherein the command data is received in the communication with the input collection/display unit, wherein the input collection/display unit is configured to capture image data of eyes of the user, to generate the command data based on the image data, and to provide the command data to the drive manager device, such that the power wheelchair is operable using the eyes of the user.

7. The power wheelchair of claim 1, wherein the buttons corresponding to controls other than the directional drive controls include at least one of:
a stop button, or
a pause button.

8. A drive manager device for managing the controls of a power wheelchair equipped with one or more motors capable of actuating a plurality of wheels, the power wheelchair being further equipped with a drive controller operatively connected to the one or more motors and to the drive manager device, the drive manager device comprising:
a set of communication interfaces;
one or more memories; and
one or more processors, operatively coupled to the one or more memories, to:
communicate with an input collection/display unit via a first wired communication interface of the set of communication interfaces, the input collection/display unit operable by a user in the power wheelchair,
determine a command made by the user by processing command data received in a communication with the input collection/display unit, the command being a request to drive the power wheelchair,
in response to determining the command, cause voltage to be applied to the drive controller via a second wired communication interface of the set of communication interfaces, wherein the voltage causes the drive controller to interact with the one or more motors to actuate one or more wheels of the plurality of wheels,
establish a communication session with a caregiver unit via a wireless communication interface, such that the input collection/display unit and the caregiver unit are permitted to engage in concurrent communications, wherein the caregiver unit is external to the power wheelchair and operable by a caregiver,
determine that the input collection/display unit is a controlling device that is presently controlling the power wheelchair, where the caregiver unit is a non-controlling device, and
cause a user interface to be provided for display on the non-controlling device such that the user interface omits buttons corresponding to directional drive controls so as to prevent the non-controlling device from driving the power wheelchair, and displays one or more buttons corresponding to controls other than the directional drive controls.

9. The drive manager device of claim 8, wherein the one or more processors are further to:
receive, from the caregiver unit, emergency stop command data associated with a command to stop the power wheelchair; and
cause voltage to be applied through the second communication interface and to the drive controller, wherein the voltage causes the drive controller to interact with the breaking component to stop the power wheelchair.

10. The drive manager device of claim 8, wherein the first wired communication interface is a universal serial bus (USB) interface, and the wireless communication interface is a Bluetooth interface.

11. The drive manager device of claim 8, wherein the one or more processors are further to:
receive, from the input collection/display unit, initial command data indicating a first command made by the user to power on the power wheelchair;
determine, by processing the initial command data, that the first command is to power on the power wheelchair; and
in response to the determined first command, cause voltage to be applied through a third wired communication interface, of the set of communication interfaces, such that power is provided to the drive controller to thereby enable the user to operate the power wheelchair.

12. A method for managing the controls of a power wheelchair equipped with one or more motors, a plurality of wheels, a drive controller operatively connected to the one or more motors and mounted to the power wheelchair, and a drive manager device operatively connected to the drive controller; the method comprising:
receiving, by the drive manager device, command data for a command to drive the power wheelchair, wherein the command data is received from an input collection/display unit via a first communication interface, the input collection/display unit being operable by a user in the power wheelchair;
determining, by the drive manager device, the command made by the user by processing the received command data;
causing, by the drive manager device, voltage to be applied through a second communication interface and to the drive controller, wherein the voltage causes the drive controller to interact with the one or more motors to actuate one or more wheels of the plurality of wheels;

establishing, by the driver manager device, a communication session with a caregiver unit via a third communication interface, wherein the caregiver unit is external to the power wheelchair and operable by a caregiver, and wherein the first communication interface and third communication interface permit the drive manager device to engage in concurrent communications with the input collection/display unit and the caregiver unit;

preventing, by the drive manager device, the caregiver unit and the input collection/display unit from controlling the power wheelchair concurrently, determining, by the drive manager device, that the input collection/display unit is a controlling device that is presently controlling the power wheelchair, where the caregiver unit is a non-controlling device, and causing, by the drive manager device, a user interface to be provided for display on the non-controlling device such that the user interface omits buttons corresponding to directional drive controls so as to prevent the non-controlling device from driving the power wheelchair, and displays one or more buttons corresponding to controls other than the directional drive controls.

13. The method of claim 12, further comprising:
removing control of the power wheelchair from the input collection/display unit; and
assigning control of the power wheelchair to the caregiver unit.

14. The method of claim 13, wherein assigning control of the power wheelchair to the caregiver unit comprises: assigning control based on the drive manager device receiving, from the caregiver unit, new command data associated with a request to control the power wheelchair.

15. The method of claim 12, the method further comprising:
receiving, from the caregiver unit, emergency stop command data associated with a command to stop the power wheelchair; and
causing voltage to be applied through the second communication interface and to the drive controller, wherein the voltage causes the drive controller to interact with a breaking component to stop the power wheelchair.

16. The method of claim 12, further comprising:
receiving, from the input collection/display unit, initial command data indicating a first command made by the user to power on the power wheelchair;
determining, by processing the initial command data, that the first command is to power on the power wheelchair; and
in response to determining that the first command is to power on the power wheelchair, causing voltage to be applied through a fourth communication interface such that power is provided to the drive controller to thereby enable the user to operate the power wheelchair.

17. The method of claim 12, further comprising:
receiving, by the drive manager device and from the caregiver unit via the communication session, emergency stop command data associated with a command to stop the power wheelchair; and
causing, by the drive manager device, voltage to be applied through the third communication interface and to the drive controller such that the drive controller interacts with a breaking component to stop the power wheelchair.

* * * * *